United States Patent
Feng

(10) Patent No.: US 11,010,938 B2
(45) Date of Patent: May 18, 2021

(54) SYSTEMS AND METHODS FOR POSITRON EMISSION TOMOGRAPHY IMAGE RECONSTRUCTION

(71) Applicant: UIH AMERICA, INC., Houston, TX (US)

(72) Inventor: Tao Feng, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 117 days.

(21) Appl. No.: 16/374,672

(22) Filed: Apr. 3, 2019

(65) Prior Publication Data
US 2020/0320753 A1   Oct. 8, 2020

(51) Int. Cl.
*G06T 11/00* (2006.01)
*A61B 5/00* (2006.01)
*A61B 6/03* (2006.01)

(52) U.S. Cl.
CPC .......... *G06T 11/008* (2013.01); *A61B 5/7267* (2013.01); *A61B 6/037* (2013.01); *G06T 2210/41* (2013.01); *G06T 2211/424* (2013.01)

(58) Field of Classification Search
None
See application file for complete search history.

(56) References Cited
U.S. PATENT DOCUMENTS
2017/0372497 A1\* 12/2017 Hu .................... G06T 5/007
\* cited by examiner

*Primary Examiner* — Leon Flores
(74) *Attorney, Agent, or Firm* — Metis IP LLC

(57) ABSTRACT

Methods and systems for PET image reconstruction are provided. A method may include obtaining an image sequence associated with a subject. The image sequence may include one or more images generated via scanning the subject at one or more consecutive time periods. The method may also include obtaining a target machine learning model. The method may further include generating at least one target image using the target machine learning model based on the image sequence. The at least one target image may present a dynamic parameter associated with the subject. The target machine learning model may provide a mapping between the image sequence and the at least one target image.

20 Claims, 12 Drawing Sheets

SYSTEMS AND METHODS FOR POSITRON EMISSION TOMOGRAPHY IMAGE RECONSTRUCTION

TECHNICAL FIELD

This disclosure generally relates to Positron Emission Tomography (PET) technology, and more particularly, to methods and systems for image reconstruction.

BACKGROUND

Positron Emission Tomography (PET) systems are widely used in medical diagnosis. Using a PET system, a biologically active molecule carrying a radioactive tracer is first introduced into a patient's body. The PET system then detects radiation (also referred to as PET scan data) emitted by the radioactive tracer and constructs an image of the radioactive tracer concentration within the body by analyzing detected signals. Because the biologically active molecules are natural substrates of metabolism at a target organ or tissue, a parametric image reconstructed based on the PET scan data, whose voxels or pixels presenting a value of some physiological parameter (also referred to as dynamic parameter) of tracer kinetics, can aid the evaluation of the physiology (functionality) and/or anatomy (structure) of the target organ or tissue, as well as its biochemical properties. At present, a parametric image may be reconstructed using an indirection reconstruction algorithm (e.g., a Patlak model), a direct reconstruction algorithm (e.g., a four-dimensional reconstruction model), etc. Using the indirection reconstruction algorithm, a portion of PET scan data may be used to reconstruction an image frame, which may increase noises in a reconstructed image, and decrease image quality. Using the direct reconstruction algorithm, the four-dimensional reconstruction model is complex, which may need more iterations and decrease reconstruction speed. Thus, it is desirable to provide systems and methods for reconstructing a parametric image with improved quality and reconstruction speed.

SUMMARY

In a first aspect of the present disclosure, a system for image reconstruction is provided, The system may include at least one storage device and at least one processor. The at least one storage medium may store executable instructions. The at least one processor may be configured to be in communication with the at least one storage device, wherein when executing the executable instructions, the system is configured to perform one or more of the following operations. The system may obtain an image sequence associated with a subject, The image sequence may include one or more images generated via scanning the subject at one or more consecutive time periods, The system may obtain a target machine learning model. The system may generate, based on the image sequence, at least one target image using the target machine learning model. The at least one target image may present a dynamic parameter associated with the subject. The target machine learning model may provide a mapping between the image sequence and the at least one target image.

In some embodiments, the system may input the image sequence associated with the subject into the target machine learning model. The system may convert the image sequence into the at least one target image.

In some embodiments, the system may obtain a plasma time activity curve associated with the subject. The system may generate the at least one target image by inputting the image sequence and the plasma time activity curve associated with the subject into the target machine learning model.

In some embodiments, the system may obtain, based on the image sequence, the plasma time activity curve associated with the subject using an additional target machine learning model. The additional target machine learning model may provide a mapping between the image sequence and the plasma time activity curve.

In some embodiments, a determination of the target machine learning model may include: obtaining multiple groups of training data associated one or more samples, each group of the multiple groups of training data including a first image sequence and a reference parametric image corresponding to the first image sequence, the reference parametric image presenting the dynamic parameter associated with one of the one or more samples; and generating the target machine learning model by training a machine learning model using the multiple groups of training data.

In some embodiments, the system may, for each group of the multiple group of training data, obtain projection data associated with the one of the one or more samples. The system may generate, based on the projection data the first image sequence using a first image reconstruction algorithm. The system may generate, based on the projection data the first parametric image using a second image reconstruction algorithm.

In some embodiments, the second image reconstruction algorithm may include a four-dimensional (4D) iteration technique.

In some embodiments, the determination of the target machine learning model may further include: obtaining a reference plasma time activity curve associated with the one of the one or more samples. The generating the target machine learning model by training the machine learning model using the multiple groups of training data may include: training, based on the reference plasma time activity curve, the machine learning model using the multiple groups of training data.

In some embodiments, the reference plasma time activity curve associated with the one of the one or more samples may be determined based on the image sequence associated with the one of the one or more samples.

In some embodiments, the determination of the target machine learning model may further include: obtaining multiple groups of validation data, each group of the multiple groups of validation data including a second image sequence and a second parametric image corresponding to the second image sequence, the second parametric image presenting the dynamic parameter; and adjusting the target machine learning model using the multiple groups of validation data.

In some embodiments, the target machine learning model may be constructed based on a deep learning neural network model.

In some embodiments, the deep learning neural network model may include a convolution neural network (CNN) model.

In a second aspect of the present disclosure, a method for image reconstruction is provided. The method may be implemented on a computing apparatus, the computing apparatus including at least one processor and at least one storage device. The method may include one or more of the following operations. The method may include obtaining an image sequence associated with a subject. The image sequence may include one or more images generated via scanning the subject at one or more consecutive time periods. The method may also include obtaining a target machine learning model. The method may further include generating at least one target image using the target machine learning model based on the image sequence. The at least one target image may present a dynamic parameter associated with the subject. The target machine learning model may provide a mapping between the image sequence and the at least one target image.

In a third aspect of the present disclosure, a non-transitory computer readable medium is provided. The non-transitory computer readable medium may include at least one set of instructions that, when executed by at least one processor, cause the at least one processor to effectuate a method. The method may include one or more of the following operations. The at least one processor may obtain an image sequence associated with a subject. The image sequence may include one or more images generated via scanning the subject at one or more consecutive time periods. The at least one processor may obtain a target machine learning model. The at least one processor may generate, based on the image sequence, at least one target image using the target machine learning model. The at least one target image may present a dynamic parameter associated with the subject. The target machine learning model may provide a mapping between the image sequence and the at least one target image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
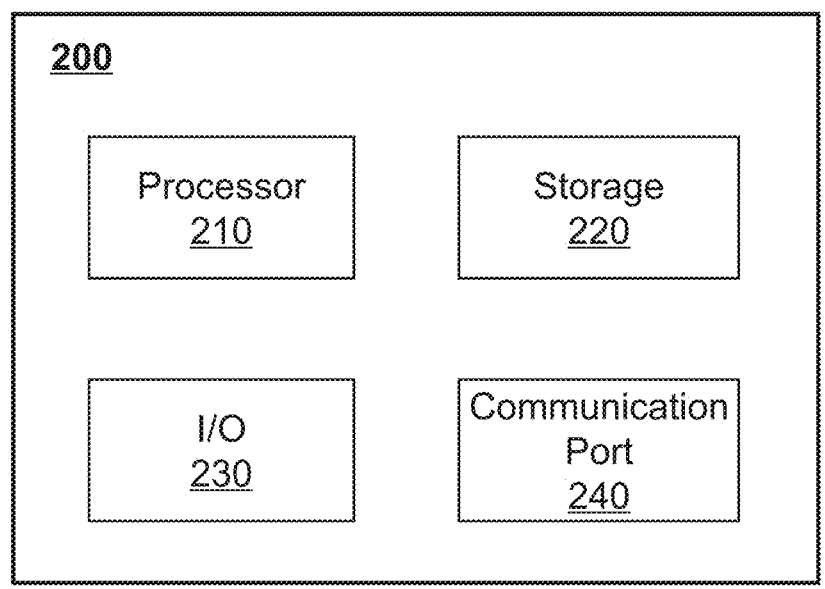
FIG. 2 is a schematic diagram illustrating hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for determining a parametric image in a PET imaging system. As used herein, the parametric image may include voxels or pixels whose value presenting a value of a physiological parameter (also referred to as dynamic parameter) of tracer kinetics. The parametric image may aid the evaluation of the physiology (functionality) and/or anatomy (structure) of the target organ or tissue, as well as its biochemical properties. To this end, a system may obtain an image sequence associated with a subject. The image sequence may include one or more images generated via scanning the subject at one or more consecutive time periods. The one or more images may be one or more standardized uptake value (SUV) images. The system may obtain a target machine learning model. The target machine learning model may be obtained by training a machine learning model using a training set and a validation set. The target machine learning model may provide a mapping relationship between the image sequence and at least one corresponding parametric image. The system may generate, based on the image sequence, at least one parametric image using the target machine learning model. The at least one parametric image may present a dynamic parameter associated with the subject. Using the target machine model for parametric image reconstruction, an image sequence may be inputted the target machine learning model and a parametric image may be output, which may improve reconstruction speed. The target machine learning model may be trained for learning to analyze and extract information presented in the inputted data to generate a parametric image, which may improve quality of the generated parametric image.

Figure 1:
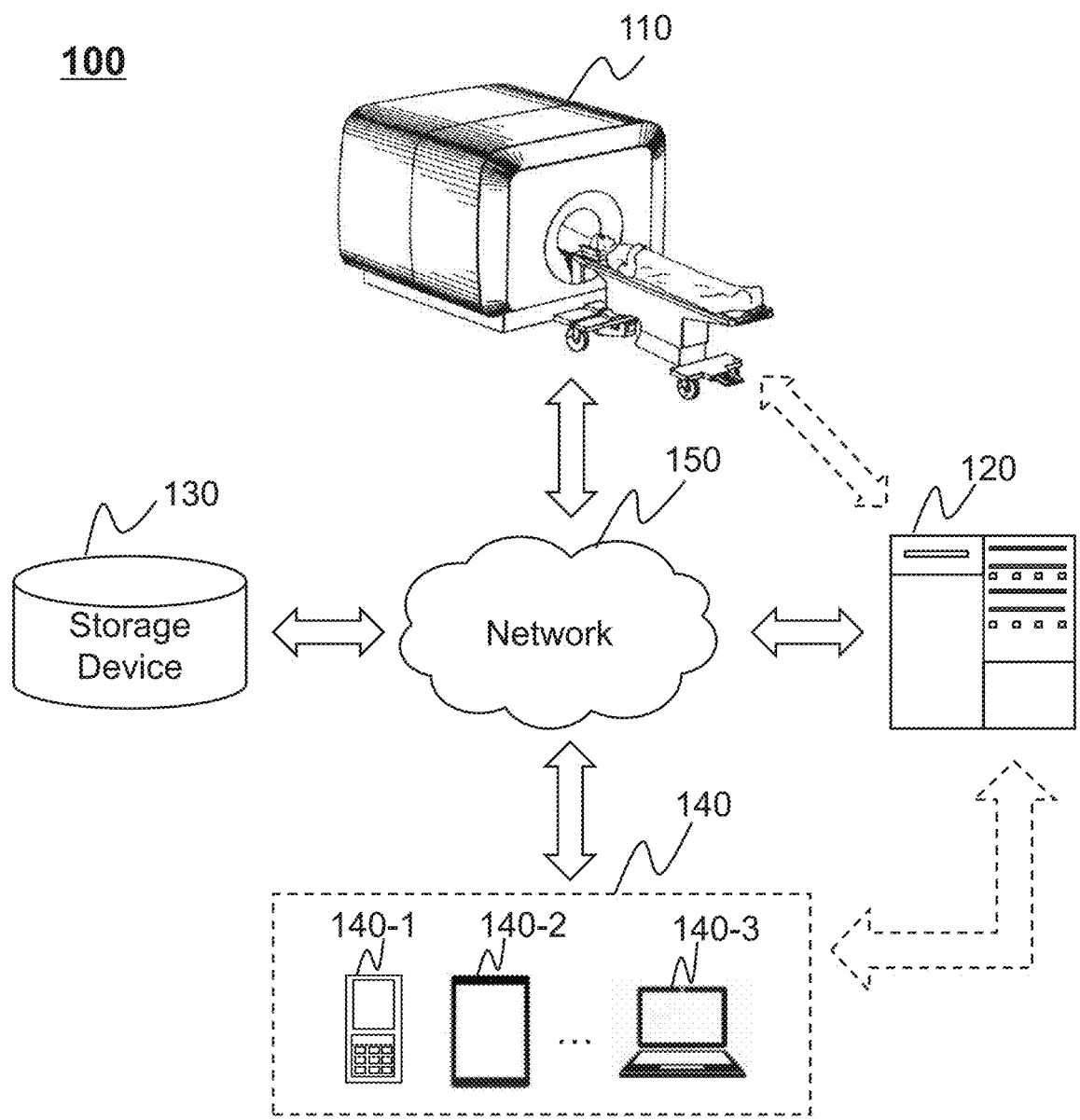
FIG. 1 is a schematic diagram illustrating an exemplary imaging system according to some embodiments of the present disclosure.

FIG. 1 is a schematic diagram illustrating an exemplary the imaging system 100 according to some embodiments of the present disclosure. The imaging system 100 may be a single-modality system. Exemplary single-modality system may include a single-photon emission computed tomography (SPECT) system, a positron emission computed tomography (PET) system, etc. The imaging system 100 may also be a multi-modality system. Exemplary multi-modality systems may include a computed tomography-positron emission tomography (CT-PET) system, a magnetic resonance-positron emission tomography (MR-PET) system, etc. In some embodiments, the multi-modality imaging system may include modules and/or components for performing emission computed tomography imaging and/or related analysis.

For illustration purposes, as shown in FIG. 1, the imaging system 100 may include a scanner 110, a processing device 120, a storage device 130, one or more terminals 140, and a network 150. The components in the imaging system 100 may be connected in one or more of various ways. Merely by way of example, the scanner 110 may be connected to the processing device 120 through the network 150. As another example, the scanner 110 may be connected to the processing device 120 directly. As a further example, the terminals) 140 may be connected to another component of the imaging system 100 (e.g., the processing device 120) via the network 150 as illustrated in FIG. 1. As still a further example, the terminal(s) 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The scanner 110 may scan at least part of a subject, and/or generate data relating to the subject. In some embodiments, the scanner 110 may be an imaging device, for example, a PET device, a PET-CT device, a PET-MRI device, etc. In the present disclosure, "object" and "subject" are used interchangeably. The subject may be biological or non-biological. For example, the subject may include a patient, a man-made object, etc. As another example, the subject may include a specific portion, organ, and/or tissue of the patient. For example, the subject may include the head, the brain, the neck, the body, a shoulder, an arm, the thorax, the heart, the stomach, a blood vessel, a soft tissue, a knee, a foot, or the like, or a combination thereof, of the patient.

The scanner 110 may include a gantry, a detector, an electronics module, a table, and/or other components not shown, for example a cooling assembly. The scanner 110 may scan a subject and obtain information related with the subject. The gantry may support components (e.g., the detector) necessary to produce and detect radiation events to generate an image. The table may position a subject in a detection region. The detector may detect radiation events (e.g., gamma photons) emitted from the detection region. In some embodiments, the detector may include a plurality of detector units. The detector units may be implemented in a suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. The electronics module may collect and/or process electrical signals (e.g., scintillation pulses) generated by the detector. The electronics module may include an adder, a multiplier, a subtracter, an amplifier, a drive circuit, a differential circuit, a integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. In some embodiments, the detected radiation events may be stored or archived in a storage (e.g., the storage device 130), displayed on a display (e.g., a screen on a computing device), or transferred to a connected device (e.g., an external database). In some embodiments, a user may control the scanner 110 via a computing device.

The processing device 120 may process data and/or information obtained from the scanner 110, the terminal(s) 140, and/or the storage device 130. For example, the processing device 120 may obtain an image sequence associated with a subject. The image sequence including one or more images generated via scanning the subject at one or more consecutive time periods by the scanner 110. As another example, the processing device 120 may obtain a target machine learning model. The target machine learning model may provide a mapping between the image sequence and at least one target image. As still an example, the processing device 120 may generate, based on the image sequence, the at least one target image using the target machine learning model. The at least one target image may present a dynamic parameter associated with the subject. In some embodiments, the processing device 120 may obtain the target machine learning model by training a machine learning model using a plurality of groups of training data (i.e., training set). The target machine learning model may be updated from time to time, e.g., periodically or not, based on training data that is at least partially different from the original training set from which the target machine learning model is determined. For instance, the target machine learning model may be updated based on a training set including new training data that are not in the original training set. In some embodiments, the determination and/or updating of the target machine learning model may be performed on a processing device, while the application of the target machine learning model may be performed on a different processing device. In some embodiments, the determination and/or updating of the target machine learning model may be performed on a processing device of a system different than the imaging system 100 on which the application of the target machine learning model is performed. For instance, the determination and/or updating of the target machine learning model may be performed on a first system of a vendor who provides and/or maintains such a machine learning model and/or has access to training samples used to determine and/or update the target machine learning model, while the application of the provided machine learning model, may be performed on a second system of a client of the vendor. In some embodiments, the determination and/or updating of the target machine learning model may be performed online in response to a request for image reconstruction. In some embodiments, the determination and/or updating of the target machine learning model may be performed offline. In some embodiments, a reconstructed image may be transmitted to the terminal(s) 140 and displayed on one or more display devices in the terminal(s) 140. In some embodiments, the processing device 120 may be a single server or a server group. The server group may be centralized or distributed. In some embodiments, the processing device 120 may be local or remote. For example, the processing device 120 may access information and/or data stored in the scanner 110, the terminal(s) 140, and/or the storage device 130 via the network 150. As another example, the processing device 120 may be directly connected to the scanner 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as illustrated in FIG. 2.

The storage device 130 may store data, instructions, and/or any other information. In some embodiments, the storage device 130 may store data obtained from the terminal(s) 140 and/or the processing device 120. For example, the storage device 130 may store PET scan data obtained from the scanner 110. As another example, the storage device 130 may store a target machine learning model as described elsewhere in the present disclosure (e.g., FIG. 7 and the descriptions thereof). In some embodiments, the storage device 130 may store data and/or instructions that the processing device 120 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components of the imaging system 100 (e.g., the processing device 120, the terminal(s) 140). One or more components of the imaging system 100 may access the data or instructions stored in the storage device 130 via the network 150. In some embodiments, the storage device 130 may be directly connected to or communicate with one or more other components of the imaging system 100 (e.g., the processing device 120, the terminal(s) 140). In some embodiments, the storage device 130 may be part of the processing device 120.

Figure 3:
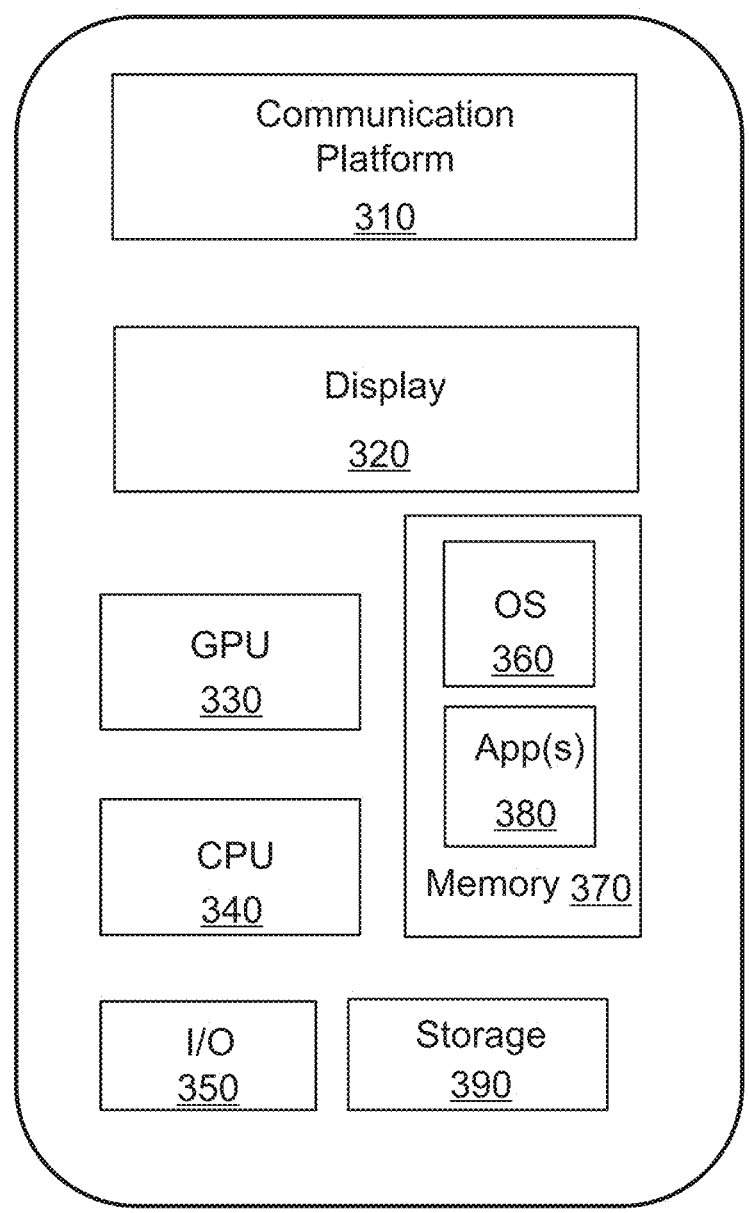
FIG. 3 is a schematic diagram illustrating hardware and/or software components of an exemplary mobile device according to some embodiments of the present disclosure.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. Merely by way of example, the terminal(s) 140 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google GlassT™, an Oculus Rift™, a Hololens™, a Gear VR™, etc. In some embodiments, the terminal(s) 140 may be part of the processing device 120.

In some embodiments, the terminal(s) 140 may send and/or receive information for parametric image reconstruction to the processing device 120 via a user interface. The user interface may be in the form of an application for parametric image reconstruction implemented on the terminal(s) 140. The user interface implemented on the terminal(s) 140 may be configured to facilitate communication between a user and the processing device 120. In some embodiments, a user may input a request for parametric image reconstruction via the user interface implemented on the terminal(s) 140. The terminal(s) 140 may send the request for parametric image reconstruction to the processing device 120 for reconstructing a parametric image based on a target machine learning model as described elsewhere in the present disclosure (e.g., FIG. 5 and the descriptions thereof). In some embodiments, the user may input and/or adjust parameters (e.g., weights) of the target machine learning model via the user interface. In some embodiments, the user interface may facilitate the presentation or display of information and/or data (e.g., a signal) relating to parametric image reconstruction received from the processing device 120. For example, the information and/or data may include a result generated by the processing device 120 in an image reconstruction. For example, the result may include one or more images (e.g., 2D images, 3D images, etc.), one or more data figures, one or more words, one or more digits, one or more models for parametric image reconstruction, parameters used in such image reconstruction, etc. In some embodiments, the information and/or data may be further configured to cause the terminal(s) 140 to display the result to the user.

The network 150 may include any suitable network that can facilitate the exchange of information and/or data for the imaging system 100. In some embodiments, one or more components of the imaging system 100 (e.g., the scanner 110, the terminal(s) 140, the processing device 120, the storage device 130, etc.) may communicate information and/or data with one or more other components of the imaging system 100 via the network 150. For example, the processing device 120 may obtain image data from the scanner 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

The network 150 may include any suitable network that can facilitate the exchange of information and/or data for the imaging system 100. In some embodiments, one or more components of the imaging system 100 (e.g., the scanner 110, the terminal(s) 140, the processing device 120, the storage device 130, etc.) may transmit or receive information and/or data with one or more other components of the imaging system 100 via the network 150. For example, the processing device 120 may obtain image data from the scanner 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected with the network 150 to exchange data and/or information.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the scanner 110, the terminals) 140, the storage device 130, and/or any other component of the imaging system 100. Specifically, the processor 210 may process one or more measured data sets (e.g., PET scan data) obtained from the scanner 110. For example, the processor 210 may reconstruct an image based on the data set(s). In some embodiments, the reconstructed image may be stored in the storage device 130, the storage 220, etc. In some embodiments, the reconstructed image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for reconstructing a dynamic parameter image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the scanner 110, the terminals) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

Figure 4:
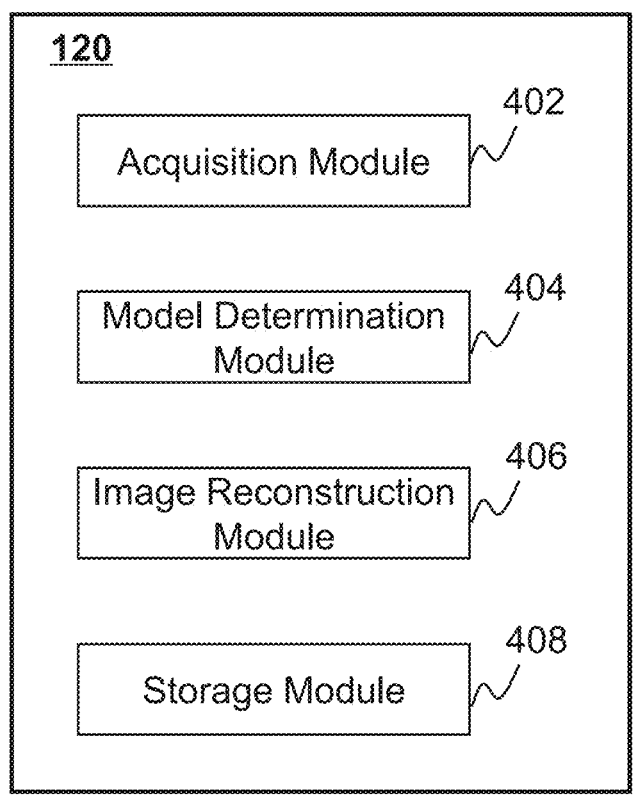
FIG. 4 is a block diagram illustrating an exemplary processing device according to some embodiments of the present disclosure.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general opera- FIG. 4 is a block diagram illustrating an exemplary processing device 120 according to some embodiments of the present disclosure. The processing device 120 may include an acquisition module 402, a model determination module 404, an image reconstruction module 406, and a storage module 408. At least a portion of the processing device 120 may be implemented on a computing device as illustrated in FIG. 2 or a mobile device as illustrated in FIG. 3.

The acquisition module 402 may obtain an image sequence associated with a subject. The acquisition module 402 may obtain the image sequence from the scanner 110, the processing device 120, one or more storage devices disclosed in the present disclosure (e.g., the storage device 130), etc. In some embodiments, the image sequence may include one or more images. An image in the image sequence may be a PET image with voxels or pixels presenting standardized uptake value (SUV) of a tracer (also referred to as SUV image). In some embodiments, the one or more images may be reconstructed independently using PET scan data acquired during each of one or more consecutive time periods. In some embodiments, the one or more images may be reconstructed dependently using PET scan data acquired during the one or more consecutive time periods.

In some embodiments, the acquisition model 402 may obtain a plasma time activity curve (TAC) associated with the subject. The plasma TAC may be denoted by a function that the concentration of radioactivity of the tracer in the plasma changes with time. In some embodiments, the acquisition model 402 may determine the plasma TAC of the subject using a golden standard technique, an arterialization of venous blood technique, a PET blood pool scan technique, a standard input function technique, a fitting function technique, or the like, or a combination thereof., as described elsewhere in the present disclosure.

In some embodiments, the acquisition module 402 may send the image sequence and/or the plasma TAC to other modules and/or units of the processing device 120 for further processing. For example, the image sequence may be sent to the storage module 408 for storage. For another example, the acquisition module 402 may send the image sequence and/or the plasma TAC to the image reconstruction module 406 for reconstructing an image. In some embodiments, the acquisition module 402 may obtain one or more machine learning models. For example, the acquisition module 402 may obtain a target machine learning model configured to, for example, generate at least one target image presenting a dynamic parameter based on the image sequence.

The model determination module 404 may determine one or more machine learning models. For example, the model determination module 404 may determine a target machine learning model configured to, for example, generate at least one target image presenting a dynamic parameter based on the image sequence obtained by the acquisition module 402. The target machine learning model may map a specific image sequence associated with a specific subject to a specific target image presenting a dynamic parameter associated with the specific subject. In some embodiments, the target machine learning model may be configured to map the specific image sequence to the specific target image based on a specific plasma TAC associated with the specific subject. For example, the target machine learning model may provide a mapping relationship between a specific image sequence, a specific plasma TAC, and a specific target image presenting a dynamic parameter associated with a specific subject.

In some embodiments, the model determination module 404 may transmit a determined target machine learning model to one or more other modules for further processing or application. For example, the model determination module 404 may transmit a target machine learning model to the storage module 408 for storage. As another example, the model determination module 404 may transmit a target machine learning model to the image reconstruction module 406 for image processing.

The image reconstruction module 406 may process information provided by various modules of the processing device 120. The image reconstruction module 406 may process an image sequence acquired by the acquisition module 402, an image sequence retrieved from the storage module 408, etc. In some embodiments, the image reconstruction module 406 may reconstruct a target image based on the image sequence according to a reconstruction technique, generate a report including one or more images and/or other related information, and/or perform any other function for image reconstruction in accordance with various embodiments of the present disclosure.

The image reconstruction module 406 may generate at least one target image based on the image sequence obtained by the acquisition module 402 and a target machine learning model determined by the model determination module 404. For example, the image sequence may be inputted into the target machine learning model. The at least one target image may be generated by the target machine learning model based on the inputted image sequence. In some embodiments, the image reconstruction module 406 may also reconstruct the at least one target image based on the plasma TAC. For example, the plasma TAC and the image sequence may be inputted into the target machine learning model. The target machine learning model may convert the image sequence into the at least one target image based on the specific plasma TAC.

The storage module 408 may store information. The information may include programs, software, algorithms, machine learning models, image data, control parameters, processed image data, or the like, or a combination thereof. For example, the information may include an image sequence, at least one target image, a plasma TAC, a target machine learning model, etc. In some embodiments, the storage module 408 may store one or more programs and/or instructions that may be executed by the processor(s) of the processing device 120 to perform exemplary methods described in this disclosure. For example, the storage module 408 may store program(s) and/or instruction(s) that can be executed by the processor(s) of the processing device 120 to acquire image data, reconstruct an image based on the image data, train a machine learning model, and/or display any intermediate result or a resultant image.

In some embodiments, one or more modules illustrated in FIG. 4 may be implemented in at least part of the exemplary imaging system 100 as illustrated in FIG. 1. For example, the acquisition module 402, the storage module 408, the model determination module 404, and/or the image reconstruction module 406 may be integrated into a console (not shown). Via the console, a user may set parameters for scanning a subject, controlling imaging processes, controlling parameters for reconstruction of an image, viewing reconstructed images, etc. In some embodiments, the console may be implemented via the processing device 120 and/or the terminal(s) 140. In some embodiments, the model determination module 404 may be integrated into the terminals) 140.

In some embodiments, the processing device 120 does not include the model determination module 404. One or more target machine learning models determined by another device may be stored in the imaging system 100 (e.g., the storage device 130, the storage 220, the storage 390, the memory 370, the storage module 408, etc.) or in an external device accessible by the processing device 120 via, for example, the network 150. In some embodiments, such a device may include a portion the same as or similar to the model determination module 404. In some embodiments, the model determination module 404 may store one or more target machine learning models determined by another device and be accessible by one or more components of the imaging system 100 (e.g., the image reconstruction module 406, etc.). In some embodiments, a target machine learning model applicable in the present disclosure may be determined by the imaging system 100 (or a portion thereof including, e.g., the processing device 120) or an external device accessible by the imaging system 100 (or a portion thereof including, e.g., the processing device 120) following the processes disclosure herein.

Figure 5:
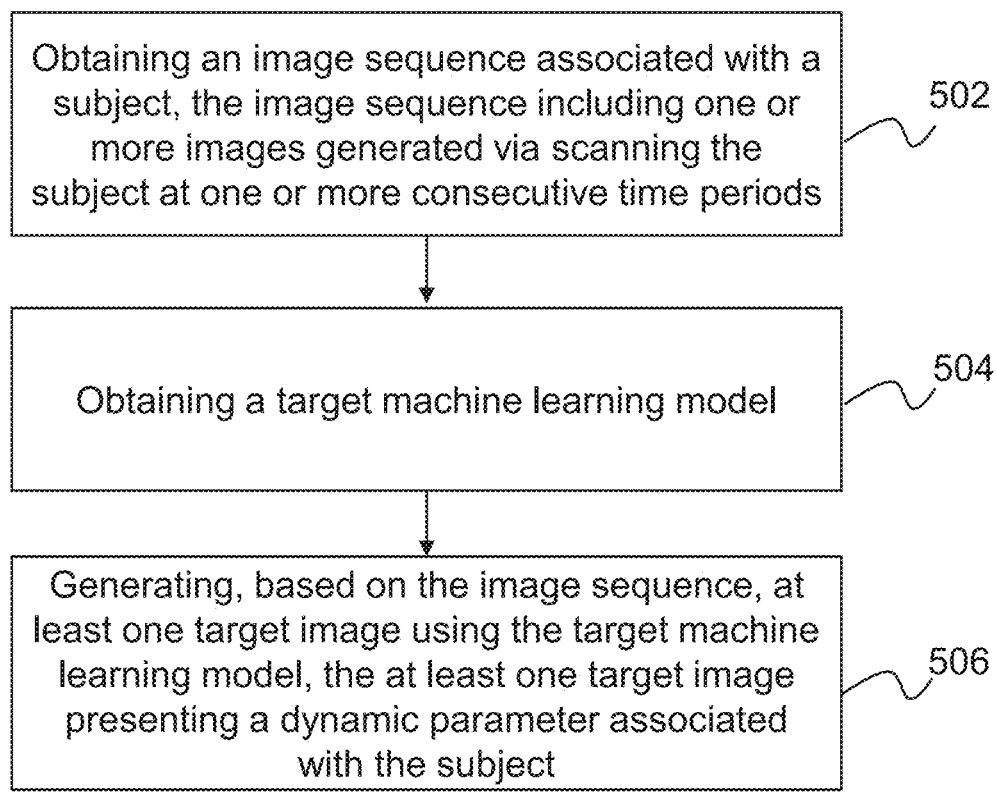
FIG. 5 is a flowchart illustrating an exemplary process for reconstructing an image according to some embodiments of the present disclosure.

FIG. 5 is a flowchart illustrating an exemplary process 500 for reconstructing an image according to some embodiments of the present disclosure. In some embodiments, one or more operations of process 500 illustrated in FIG. 5 may be implemented in the imaging system 100 illustrated in FIG. 1. For example, process 500 illustrated in FIG. 5 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 502, an image sequence associated with a subject may be obtained, the image sequence including one or more images generated via scanning the subject at one or more consecutive time periods. Operation 502 may be performed by the acquisition module 402. In some embodiments, the image sequence may be obtained from the scanner 110, the processing device 120, one or more storage devices disclosed in the present disclosure (e.g., the storage device 130), etc. The one or more images in the image sequence may be also referred to as dynamic activity images of the subject, which may present a dynamic change of uptake of a tracer (or radioactive tracer) in one or more ROIs of the subject (e.g., a tumor) with time. An image in the image sequence may be a standardized uptake value (SUV) image with voxels or pixels presenting SUV associated with one or more regions of interests (ROIs) of the subject. A SUV associated with an ROI may represent an uptake of a tracer (or radioactive tracer) of the ROI in the subject (e.g., a tumor) that is normalized by an injected dose of the tracer and a body mass (or body surface area) of the subject. A SUV associated with an ROI may be used to characterize the ROI. For example, if the SUV of the ROI is greater than a threshold, the ROI may be identified and/or determined as a tumor.

In some embodiments, the one or more images in the image sequence may be reconstructed independently using PET scan data acquired during each of the one or more consecutive time periods. A specific SUV image corresponding to a specific time period may be reconstructed based on PET scan data acquired during a specific time period using an image reconstruction algorithm. Exemplary image reconstruction algorithms may include an iterative algorithm, an analysis algorithm, etc. The iterative algorithm may include a Maximum Likelihood Estimation Method (MLEM) algorithm, an ordered subset expectation maximization (OSEM), a 3D reconstruction algorithm, etc. The analysis algorithm may include a filtered back projection (FBP) algorithm. The PET scan data associated with the specific image may be obtained by a PET scanner (e.g., the scanner 110) by way of scanning the subject (e.g., a substance, an organ, a tissue, etc.) during the specific time period. Typically, the PET scan data may include raw data (e.g., coincidence events) collected during the PET scanning, projection data, etc. The projection data may be generated by processing the raw data by a processing device (e.g., the processing device 120). The projection data may be stored as a sinogram via a histogram-mode acquisition, or stored as a list mode file via a list-mode acquisition.

In some embodiments, each of the one or more images in the image sequence may be reconstructed using all PET scan data acquired during the one or more consecutive time periods. The one or more images may be reconstructed using, for example, an iterative temporal smoothing model, an advanced temporal basis function, a principal components transformation of dynamic data, a wavelet-based model, or the like, or any combination.

As used herein, the one or more consecutive time periods may refer to time periods after a time interval after the injection of a tracer. The time interval may be set by a user or according to a default setting of the imaging system 100, or may be adjustable under different situations. For example, the time interval may be 30 min, 40 min, etc. The time length of each of the one or more consecutive time periods may be set by a user or according to a default setting of the imaging system 100, or may be adjustable under different situations. For example, the time length may be 10 min, 20 min, or the like, or any combination thereof. Taking a time interval as 30 min and a time length as 10 as an example, the first consecutive time period may be 30-40 min after the injection of the tracer, and the second consecutive time period may be 40-50 min after the injection of the tracer. During each consecutive time period, an image (i.e., a dynamic frame) may be acquired by the scanner 110 scanning the subject.

In 504, a target machine learning model may be obtained. Operation 504 may be performed by the model determination module 404. The target machine learning model may be configured to use a specific image sequence (e.g., the image sequence obtained in 502) as an input and generate a specific parametric image as an output. In some embodiments, the target machine learning model may be configured to provide a mapping relationship between a specific image sequence and a specific target image presenting a dynamic parameter associated with a specific subject. As used herein, an image presenting a dynamic parameter associated with a subject may be also referred to as a parametric image. In other words, the target machine learning model may be used to convert the specific image sequence associated with a specific subject into a specific parametric image based on the mapping relationship. For example, the image sequence obtained in 502 may be inputted to the target machine learning model. At least one target image presenting a dynamic parameter associated with the subject may be generated by the target machine learning model based on the inputted image sequence obtained in 502.

In some embodiments, the target machine learning model may be configured to map the specific image sequence to the specific parametric image based on a specific plasma time activity curve (TAC) associated with the specific subject. For example, the target machine learning model may be configured to provide a mapping relationship between a specific image sequence, a specific plasma time activity curve (TAC), and a specific target image presenting a dynamic parameter (i.e., parametric image) associated with a specific subject. The specific plasma TAC associated with the specific subject and the specific image sequence may be inputted into the target machine learning model. The target machine learning model may convert the specific image sequence into the specific parametric image of the specific subject based on the specific plasma TAC. For another example, the target machine learning model may provide a mapping relationship between the specific image sequence and the specific plasma TAC. The specific image sequence may be inputted into the target machine learning model. The target machine learning model may be used to determine the specific plasma TAC of the specific subject based on the inputted specific image sequence. Further, the target machine learning model may provide a mapping relationship between the specific image sequence, the determined specific plasma TAC, and the corresponding specific parametric image of the specific subject. Detailed descriptions regarding the plasma TACs may be found elsewhere in the present disclosure (e.g., FIG. 6 and the descriptions thereof).

The target machine learning model may be obtained from the model determination module 404, the storage device 130, or any other storage device. For example, the model determination module 404 may generate the target machine learning model by training a machine learning model based on multiple groups of training data using a model training algorithm. Exemplary model training algorithms may include a gradient descent algorithm, a Newton's algorithm, a Quasi-Newton algorithm, a Levenberg-Marquardt algorithm, a conjugate gradient algorithm, or the like, or a combination thereof. The multiple groups of training data (also referred to as training set) may be associated with one or more samples same as or different from the subject as descried in 502. Each of the multiple groups of training data may include an image sequence and a reference parametric image of a specific sample. The image sequence and the reference parametric image of the specific sample may be reconstructed based on same PET scan data using different reconstruction algorithms. In some embodiments, each group of the multiple groups of training data may include a corresponding plasma TAC associated with one of the one or more samples. More descriptions of the determination of the plasma TAC may be found elsewhere in the present disclosure (e.g., FIG. 6 and the descriptions thereof). More descriptions for the multiple groups of training data may be found elsewhere in the present disclosure (e.g., FIG. 7 and the descriptions thereof).

The machine learning model may be constructed based on a deep learning neural network model. Exemplary deep learning neural network models may include a convolutional machine learning model (CNN), a fully convolutional neural network (FCN) model, a generative adversarial network (GAN), a back propagation (BP) machine learning model, a radial basis function (RBF) machine learning model, a deep belief nets (DBN), an Elman machine learning model, or the like, or a combination thereof.

In some embodiments, the machine learning model may be constructed based on one single machine learning model. The one single machine learning model may be trained to provide the mapping relationship between the specific image sequence, the specific plasma TAC, and the corresponding specific parametric image of the specific subject, or the mapping relationship between the specific image sequence and the corresponding specific parametric image of the specific subject. In some embodiments, the one single trained machine learning model (i.e., the target machine learning model) may be configured to convert an inputted specific image sequence into a specific parametric image of a specific subject based on the mapping relationship. In some embodiments, the one single trained machine learning model (i.e., the target machine learning model) may be configured to convert an inputted specific image sequence into a specific parametric image of a specific subject based on the mapping relationship and an inputted specific plasma TAC.

In some embodiments, the machine learning model may be constructed based on at least two sub-models, e.g., a first sub-model and a second sub-model. The first sub-model may be trained to provide the mapping relationship between the specific image sequence and the specific plasma TAC of the specific subject. The trained first sub-model may be configured to convert an inputted specific image sequence into a specific plasma TAC of a specific subject. The second sub-model may be trained to provide the mapping relationship between the specific image sequence, the determined specific plasma TAC and the corresponding specific parametric image of the specific subject. The trained second sub-model may be configured to convert the inputted specific image sequence into a specific parametric image of a specific subject based on the mapping relationship and the determined specific plasma TAC. In some embodiments, the first sub-model and the second sub-model may be independent from each other. The training of the first sub-model and the second sub-model may be independent. In some embodiments, the first sub-model and the second sub-model may be connected with each other via, for example, a node, a layer, etc. The first sub-model and the second sub-model may be trained as a whole to determine the target machine learning model.

During a training process of the machine learning model, the mapping relationship between an image sequence and corresponding at least one target image may be established based on the multiple groups of training data. In some embodiments, the trained machine learning model may be determined as the target machine learning model. In some embodiments, the trained machine learning model may be adjusted and/or optimized using one or more groups of validation data. The trained machine learning model after being adjusted and/or optimized may be designated as the target machine learning model. The target machine learning model may be generated according to the exemplary process for training a machine learning model disclosed elsewhere in the present disclosure (e.g., FIGS. 7-8, the process 700 and the process 800).

In 506, at least one target image may be generated using the target machine learning model, the at least one target image presenting a dynamic parameter associated with the subject. Operation 506 may be performed by the image reconstruction module 406. In the at least one target image, each voxel or pixel may present a value of a dynamic parameter (also referred to as physiological parameter) of tracer kinetics, while the original SUV image presents radioactivity concentrations. The at least one target image may be also referred to as a target parametric image. The dynamic parameter may be configured to present the metabolism of a tracer injected into the sample. Exemplary dynamic parameters may include a perfusion rate of a tracer, a receptor binding potential of the tracer, a distribution of the tracer in the plasma, a distribution of the tracer in the sample, a transport rate of the tracer from the plasma to a tissue (i.e., K1), a transport rate of the tracer from a tissue to the plasma (i.e., K2), or the like, or any combination thereof.

In some embodiments, the at least one target image (i.e., target parametric image) may be generated by inputting the image sequence associated with the subject into the target machine learning model. The target parametric image may be an output of the target machine learning model. For example, the target machine learning model may determine and/or output the at least one target image based on the mapping relationship between the specific image sequence associated with the specific subject and the specific parametric image of the specific subject. In some embodiments, the at least one target image may be generated based on the image sequence and a corresponding plasma TAC of the subject. For example, the at least one target image may be generated by inputting the image sequence and the corresponding plasma TAC associated with the subject into the target machine learning model. Then the target machine learning model may determine the at least one target image based on the mapping relationship between the specific image sequence and the specific parametric image of the specific subject based on the plasma TAC associated with the subject. In some embodiments, the plasma TAC associated with the subject may be determined based on the image sequence. Detailed descriptions regarding the determination of the plasma TAC may be found elsewhere in the present disclosure (e.g., FIG. 6 and the descriptions thereof).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in operation 506, to generate the at least one target image with the input of the image sequence, the target machine learning model may first determine the corresponding plasma TAC based on the inputted image sequence. Then the target machine learning model may determine the at least one target image based on the corresponding plasma TAC and the image sequence. In some embodiments, process 500 may further include obtaining a plasma TAC of the subject.

Figure 6:
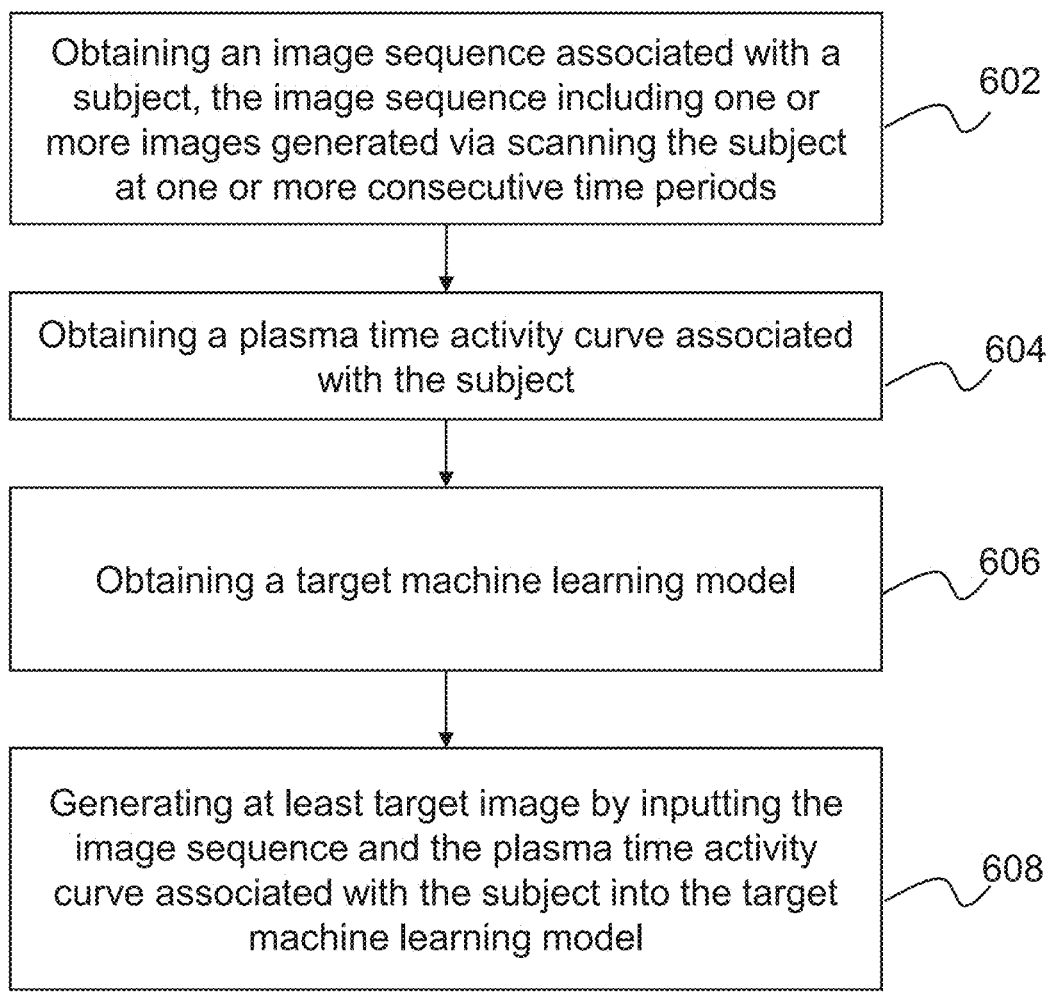
FIG. 6 is a flowchart illustrating an exemplary process for reconstructing an image according to some embodiments of the present disclosure.

FIG. 6 is a flowchart illustrating an exemplary process 600 for reconstructing an image according to some embodiments of the present disclosure. In some embodiments, one or more operations of process 600 illustrated in FIG. 6 may be implemented in the imaging system 100 illustrated in FIG. 1. For example, process 600 illustrated in FIG. 6 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 602, an image sequence associated with a subject may be obtained, the image sequence including one or more images generated via scanning the subject at one or more consecutive time periods. Operation 602 may be performed by the acquisition module 402. The image sequence may be similar to or same as that described in operation 502, and will not be repeated herein.

In 604, a plasma time activity curve (TAC) associated with the subject may be obtained. Operation 604 may be performed by the acquisition module 402. As used herein, the plasma TAC may be also referred to as a plasma input function. The plasma TAC may be denoted by a function that the concentration of radioactivity of the tracer in the plasma changes with time. The plasma TAC of the subject may be determined using a gold standard technique, an arterialization of venous blood technique, a PET blood pool scan technique, a standard input function technique, a fitting function technique, or the like, or a combination thereof. Using the golden standard technique, the arterial blood of the subject may be sampled to measure plasma TAC of the subject. Using the arterialization of venous blood technique, the venous blood of the subject may be sampled to measure plasma TAC of the subject. Using the PET blood pool scan technique, the plasma TAC of the subject may be determined based on the image sequence. For example, the processing device 120 may determine a region of interest (ROI) (e.g., a region associated with the heart or arterial blood) from each of the one or more images in the image sequence. The processing device 120 may identify a blood TAC from the one or more images based on the determined ROI and designate the blood TAC as the plasma TAC. The plasma TAC identified from the image sequence may be also referred to as an image-derived input function. Using the standard input function technique, the plasma TAC of the subject may be determined based on a plurality of plasma TACs of multiple persons (e.g., patients) determined based on the golden standard technique. Further, the plurality of plasma TACs of multiple persons may be normalized and averaged to obtain the plasma TAC of the subject. Using the fitting function technique, the plasma TAC of the subject may be determined by fitting the plurality of plasma TACs of multiple persons. The plasma TAC of the subject determined based on the plurality of plasma TACs of multiple persons may be also referred to as a population-based input function (or standard arterial input function, SAIF). In some embodiments, the plasma TAC of the subject may be determined based on the image sequence and the plurality of plasma TACs of multiple persons. The plasma TAC of the subject determined based on the image-derived input function and the population-based input function may be also referred to as a population-based input function normalized by image (also referred to as PBIFNI). For example, the plasma TAC may be determined by normalizing the population-based input function using the image-derived input function. As a further example, the processing device 120 may average the population-based input function and the image-derived input function to obtain the population-based input function normalized by image.

In some embodiments, the plasma TAC may be determined based on the image sequence using a trained machine learning model. The trained machine learning model may be configured to provide a mapping between the image sequence and the plasma TAC of the subject. The trained machine learning model may be used to determine the plasma TAC based on the mapping relationship. For example, the image sequence may be inputted into the trained machine learning model. The trained machine learning model may generate and output the plasma TAC. The trained machine learning model may be obtained from the model determination module 404, the storage device 130, or any other storage device. For example, the model determination module 404 may generate the trained machine learning model by training a machine learning model based on multiple groups of training data using a model training algorithm. Each group of the multiple groups of training data may include an image sequence and a reference plasma TAC of a sample. The reference plasma TAC of a sample may be determined according to one or more plasma TAC determination techniques as described above.

In 606, a target machine learning model may be obtained. Operation 606 may be performed by the model determination module 404. The target machine learning model may be similar to or same as that described in operation 504, and will not be repeated herein. For example, the target machine learning model may provide a mapping between a specific image sequence and a specific target image presenting a dynamic parameter associated with a specific subject (also referred to as a parametric image). In other words, the target machine learning model may be used to convert the specific image sequence associated with a specific subject into a specific parametric image. As another example, the target machine learning model may provide a mapping between a specific image sequence, a specific plasma TAC, and a specific parametric image of a specific subject. In some embodiments, the target machine learning model and the trained machine learning model as described in operation 604 may be integrated into one single model. In some embodiments, the target machine learning model and the trained machine learning model as described in operation 604 may be separate and/or independent from each other.

In 608, at least one target image may be generated by inputting the image sequence and the plasma TAC associated with the subject into the target machine learning model. Operation 608 may be performed by the image reconstruction module 406. The generation of the at least one target image by inputting the image sequence and the plasma TAC into the target machine learning model may be similar to or same as that in operation 506, and will not be repeated herein.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, process 600 may further include one or more storing operations.

Figure 7:
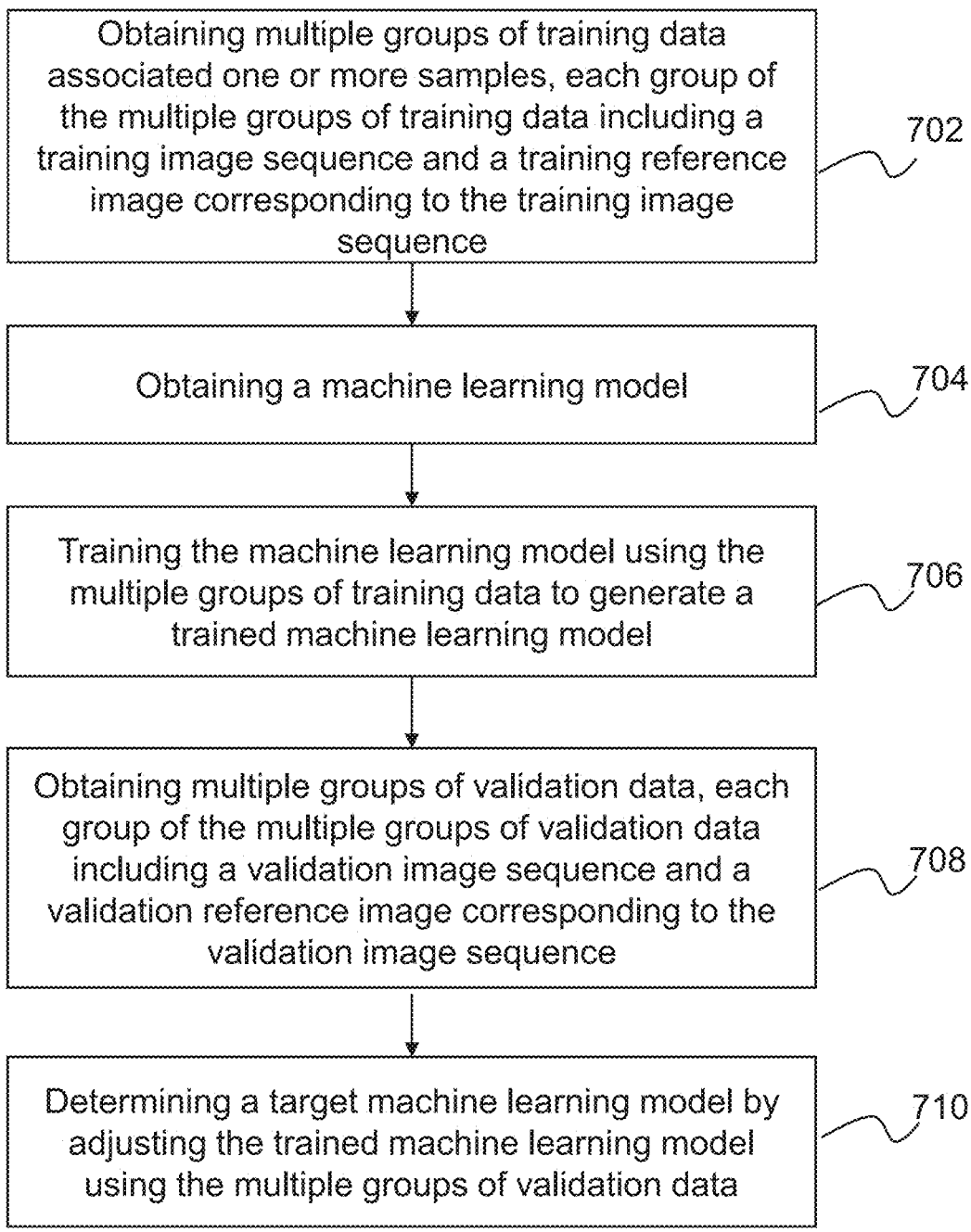
FIG. 7 is a flowchart illustrating an exemplary process for training a machine learning model according to some embodiments of the present disclosure.

FIG. 7 is a flowchart illustrating an exemplary process 700 for training a machine learning model according to some embodiments of the present disclosure. In some embodiments, one or more operations of process 700 illustrated in FIG. 7 may be implemented in the imaging system 100 illustrated in FIG. 1. For example, process 700 illustrated in FIG. 7 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). In some embodiments, one portion of operation 506 illustrated in FIG. 5 may be performed according to the process 700. For example, the target machine learning model as described in operation 506 may be determined according to process 700.

In 702, multiple groups of training data may be obtained. The multiple groups of training data may be associated with one or more samples. Operation 702 may be performed by the model determination module 404. The multiple groups of training data associated with one or more samples may form a training set. As used herein, a sample may be also referred to as a subject as described elsewhere in the present disclosure (e.g., FIG. 1 and the descriptions thereof). For example, a sample may be the entire volume of a subject, or a portion of the subject, such as the head, the thorax, the abdomen, or the like, or a combination thereof. For another example, a sample may be a specific organ, such as the heart, the esophagus, the trachea, the bronchus, the stomach, the gallbladder, the small intestine, the colon, the bladder, the ureter, the uterus, the fallopian tube, etc.

Each group of the multiple groups of training data may include an image sequence and a reference parametric image corresponding to the image sequence. An image sequence of a specific group may include dynamic activity images (e.g., one or more SUV images) associated with one of the one or more samples. The dynamic activity images (e.g., one or more SUV images) of the image sequence associated with a sample may be obtained from the scanner 110, the processing device 120, one or more storage devices disclosed in the present disclosure (e.g., the storage device 130), etc. The one or more SUV images associated with the sample may be reconstructed based on PET scan data (e.g., an original sinogram) collected during a PET scanning of the sample at one or more consecutive time periods. In some embodiments, the original sinogram may be four-dimensional (4D) data generated by processing raw data (e.g., coincidence events). The reconstruction of the one or more SUV images may be similar to or same as that of the image sequence described in connection with operation 502, and will not be repeated herein. For example, the one or more SUV images may be reconstructed using a first image reconstruction algorithm. The first image reconstruction algorithm may include an iterative algorithm, an analysis algorithm, etc. The iterative algorithm may include a Maximum Likelihood Estimation Method (MLEM) algorithm, an ordered subset expectation maximization (OSEM), a 3D reconstruction algorithm, etc. The analysis algorithm may include a filtered back projection (FBP) algorithm.

A reference parametric image of the specific group may present a dynamic parameter associated with the same sample as the image sequence of the specific group. Each voxel or pixel of a reference parametric image may represent a value of a physiological parameter (also referred to as dynamic parameter) of tracer kinetics as described elsewhere in the present disclosure (e.g., FIG. 5 and the descriptions thereof).

In some embodiments, a reference parametric image corresponding to the image sequence may be reconstructed based on the PET scan data (e.g., the original sinogram) using a second image reconstruction algorithm. The second image reconstruction algorithm may include a four-dimensional (4D) iteration technique. For example, the reference parametric image may be reconstructed based on the PET scan data (e.g., original sinogram) using the MLEM algorithm. The processing device 120 may reconstruct the reference parametric image according to Equation (2) as following:

$$K^{n+1} = K^n \frac{1}{PM} P \frac{Y}{PK^n M + S + R} M, \quad (2)$$

where K denotes a reference parametric image, Y denotes an original sinogram, M denotes a relationship between a reference parametric image and an image sequence, P denotes a projection matrix, S denotes a scatter sinogram, R denotes a random coincidences sinogram, and n denotes the count (or number) of iterations using the four-dimensional (4D) iteration technique. The projection matrix may be set by a user or according to a default setting of the imaging system 100. The scatter sinogram S and/or the random coincidence sinogram R may be determined based on original PET acquisitions (e.g., radiation events). For example, the scattering sinogram may be obtained by a scatter estimation approach such as Monte Carlo scatter estimation technique, The random coincidence sinogram may be estimated by measuring delay events.

The relationship between the reference parametric image and the image sequence M may satisfy Equation (3) as following:

$$KM=X \qquad (3),$$

where X denotes the image sequence including one or more SUV images (also referred to as dynamic activity images). According to Equations (2) and (3), the reference parametric image may be reconstructed.

In some embodiments, the second reconstruction algorithm may include a maximum likelihood expectation maximization (MLEM) algorithm, an expectation maximization (EM) algorithm, a parametric iterative coordinate descent (PICD) algorithm, using a Patlak model, or the like, or any combination thereof.

In some embodiments, each group of the multiple groups of training data may include a corresponding plasma TAC associated with one of the one or more samples. More descriptions of the determination of the plasma TAC may be found elsewhere in the present disclosure (e.g., FIG. 6 and the descriptions thereof).

In 704, a machine learning model may be obtained. Operation 704 may be performed by the model determination module 404. In some embodiments, the machine learning model may be stored in a storage device as an application or a part thereof. The machine learning model may be constructed based on at least one of a convolutional machine learning model (CNN), a fully convolutional neural network (FCN) model, a generative adversarial network (GAN), a back propagation (BP) machine learning model, a radial basis function (RBF) machine learning model, a deep belief nets (DBN) machine learning model, an Elman machine learning model, or the like, or a combination thereof. In some embodiments, the machine learning model may include multiple layers, for example, an input layer, multiple hidden layers, and an output layer. The multiple hidden layers may include one or more convolutional layers, one or more pooling layers, one or more batch normalization layers, one or more activation layers, one or more fully connected layers, a cost function layer, etc. Each of the multiple layers may include a plurality of nodes. The machine learning model may be trained to take dynamic activity images (e.g., SUV images) as an input and one or more parametric images as an output.

In some embodiments, the machine learning model may be defined by a plurality of architecture parameters and a plurality of learning parameters. The plurality of learning parameters may be altered during the training of the machine learning model using the multiple groups of training data, while the plurality of architecture parameters may not be altered during the training of the machine learning model using the multiple groups of training data. The plurality of architecture parameters may be set and/or adjusted by a user before the training of the machine learning model. Exemplary architecture parameters of the machine learning model may include the size of a kernel of a layer, the total count (or number) of layers, the count (or number) of nodes in each layer, a learning rate, a minibatch size, an epoch, etc. Exemplary learning parameters of the machine learning model may include a connected weight between two connected nodes, a bias vector relating to a node, etc. The connected weight between two connected nodes may be configured to represent a proportion of an output value of a node to be as an input value of another connected node. The bias vector relating to a node may be configured to control an output value of the node deviating from an origin.

In 706, the machine learning model may be trained using the multiple groups of training data to generate a trained machine learning model. Operation 706 may be performed by the model determination module 404. Exemplary neural network training algorithms may include a gradient descent algorithm, a Newton's algorithm, a Quasi-Newton algorithm, a Levenberg-Marquardt algorithm, a conjugate gradient algorithm, or the like, or a combination thereof, as exemplified in FIG. 9 and the description thereof. In some embodiments, the machine learning model may be trained by performing a plurality of iterations based on a cost function. Before the plurality of iterations, the plurality of learning parameters of the machine learning model may be initialized. For example, the connected weights and/or the bias vector of nodes of the machine learning model may be initialized to be random values in a range, e.g., the range from −1 to 1. As another example, all the connected weights of the machine learning model may have a same value in the range from −1 to 1, for example, 0. As still an example, the bias vector of nodes in the machine learning model may be initialized to be random values in a range from 0 to 1. In some embodiments, the plurality of learning parameters of the machine learning model may be initialized based on a Gaussian random algorithm, a Xavier algorithm, etc. Then the plurality of iterations may be performed to update the plurality of learning parameters of the machine learning model until a condition is satisfied. The condition may provide an indication of whether the machine learning model is sufficiently trained. For example, the condition may be satisfied if the value of the cost function associated with the machine learning model is minimal or smaller than a threshold (e.g., a constant). As another example, the condition may be satisfied if the value of the cost function converges. The convergence may be deemed to have occurred if the variation of the values of the cost function in two or more consecutive iterations is smaller than a threshold (e.g., a constant). As still an example, the condition may be satisfied when a specified number of iterations are performed in the training process.

For each of the plurality of iterations, an image sequence (e.g., dynamic activity images), a plasma TAC, and a reference parametric image in one group of the multiple groups of training data may be inputted into the machine learning model. The image sequence, a plasma TAC, and the reference parametric image may be processed by one or more layers of the machine learning model to generate at least one estimated parametric image (e.g., a parametric image presenting a dynamic parameter) corresponding to the image sequence. The at least one estimated parametric image may be compared with the reference parametric image corresponding to the image sequence based on the cost function of the machine learning model. The cost function of the machine learning model may be configured to assess a difference between an estimated value (e.g., the at least one estimated parametric image) of the machine learning model and a desired value (e.g., the reference parametric image). If the value of the cost function exceeds a threshold in a current iteration, the plurality of learning parameters of the machine learning model may be adjusted and updated to cause the value of the cost function (i.e., the difference between the at least one estimated parametric image and the reference parametric image) smaller than the threshold. Accordingly, in a next iteration, another group of training data may be inputted into the machine learning model to train the machine learning model as described above until the condition is satisfied. The trained machine learning model may be configured to output at least one estimated parametric image based on a mapping relationship when the specific image sequence (e.g., dynamic activity images) is inputted into the trained machine learning model. In some embodiments, the trained machine learning model may be determined based on the updated plurality of learning parameters. In some embodiments, the trained machine learning model may be transmitted to the storage device 130, the storage module 408, or any other storage device for storage.

In some embodiments, the training set of the target machine learning model may be updated based on added data (e.g., the image sequence obtained in 502 and the parametric image generated in 506) over a period of time (e.g., every other month, every two months, etc.). In some embodiments, the target machine learning model may be updated according to an instruction of a user, clinical demands, the updated training set, or a default setting of the imaging system 100. For example, the target machine learning model may be updated at set intervals (e.g., every other month, every two months, etc.). As another example, the target machine learning model may be updated based on added data in the training set of the target machine learning model over a period of time (e.g., every other month, every two months, etc.). If the quantity of the added data in the training set over a period of time is greater than a threshold, the target machine learning model may be updated based on the updated training set.

In 708, multiple groups of validation data may be obtained. The multiple groups of validation data may include data that is not included in the training set. Operation 708 may be performed by the model determination module 404. The multiple groups of validation data may form a validation set. Each group of the multiple groups of validation data may include an image sequence (e.g., dynamic activity images) as an input of the trained machine learning model and at least one reference parametric image corresponding to a same object. As used herein, an object may be also referred to as a subject as described elsewhere in the present disclosure (e.g., FIG. 1 and the descriptions thereof). An image sequence of a specific group may include one or more SUV images associated with a specific object. A reference parametric image of the specific group of validation data may present a dynamic parameter associated with the same specific object as the image sequence of the specific group of validation data. The SUV images of an image sequence in the validation set may be obtained in a similar to or same way as the SUV images in an image sequence in the training set. A reference parametric image in the validation set may be obtained in a similar to or same way as the reference parametric image in the training set. The determination of the image sequence and the reference parametric image in the validation set may be similar to or same as that described in operation 702, and will not be repeated herein. In some embodiments, each group of the multiple groups of validation data may include a corresponding plasma TAC associated with one of the one or more objects. More descriptions of the determination of the plasma TAC may be found elsewhere in the present disclosure (e.g., FIG. 6 and the descriptions thereof).

In some embodiments, the multiple groups of validation data and the multiple groups of training data may belong to a same data set. The data set may include multiple image sequences and multiple corresponding parametric images, wherein each of the multiple image sequences includes one or more SUV images. For example, 70% of the data set may be the multiple groups of training data, and 20% of the data set may be the multiple groups of validation data.

In 710, a target machine learning model may be determined by adjusting the trained machine learning model using the multiple groups of validation data. Operation 710 may be performed by the model determination module 404. The trained machine learning model may be adjusted and/or optimized based on the status of the trained machine learning model (e.g., underfitting, overfitting). The trained machine learning model may be adjusted by adjusting the plurality of architecture parameters based on the validation set if the trained machine learning model is underfitting or overfitting; otherwise, the trained machine learning model determined in operation 706 may be designated as the target machine learning model.

In response to determining that the trained machine learning model is underfitting, multiples operations, such as increasing the complexity of the machine learning model (e.g., by increasing the number of layers, increasing the size of a convolutional kernel, increasing the number of nodes in each layer), and decreasing the learning rate, may be adopted. In response to determining that the trained machine learning model is overfitting, multiples operations, such as decreasing the complexity of the machine learning model (e.g., by decreasing the number of layers, decreasing the number of the size of a convolutional kernel, decreasing the number of layers, decreasing the number of nodes in each layer), decreasing the learning rate, and decreasing the value of the epoch, may be adopted.

The status of the trained machine learning model may be determined based on an accuracy over the validation set and/or an accuracy over the training set. As used herein, the accuracy of the trained machine learning model may be defined by a similarity between an estimated value (e.g., an estimated parametric image) and a desired value (e.g., a reference parametric image in a group of validation data or training data). For example, an image sequence and a plasma TAC in a specific group of validation data may be inputted into the trained machine learning model. The trained machine learning model may generate and/or outputted an estimated parametric image based on the inputted image sequence and the plasma TAC. The similarity between the estimated parametric image and a reference validation image in the specific group of validation data may be determined. The greater the similarity is, the higher the accuracy of the trained machine learning model may be. The trained machine learning model may be overfitting if the accuracy over the validation set is lower than the accuracy over the training set. For example, when the accuracy over the training set increases, but the accuracy over the validation set stays the same or decreases, it may be determined that the trained machine learning model is overfitting. The trained machine learning model may be underfitting if the accuracy over the validation set is higher than the accuracy over the training set.

In some embodiments, if the accuracy of the trained machine learning model determined based on the validation set exceeds a threshold, the trained machine learning model may be determined as the target machine learning model. If the accuracy of the trained machine learning model determined based on the validation set is small than the threshold, the trained machine learning model may be adjusted to increase the accuracy of the trained machine learning model.

In some embodiments, after the trained machine learning model is adjusted, the adjusted trained machine learning model may be further trained by the training set as described in operation 706. The target machine learning model may be determined unless the newly trained machine learning model is either overfitting nor underfitting, using a newly validation set. In some embodiments, the target machine learning model may be transmitted to the storage device 130, the storage module 408, or any other storage device for storage.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the corresponding plasma TACs may be not inputted into the machine learning model along with the image sequence. In some embodiments, before generating the at least one estimated parametric image, a plasma TAC corresponding to the image sequence may be determined as described elsewhere in the present disclosure. The corresponding plasma TAC, along with the image sequence, may be processed by the machine learning model to generate the at least one estimated parametric image.

Figure 8:
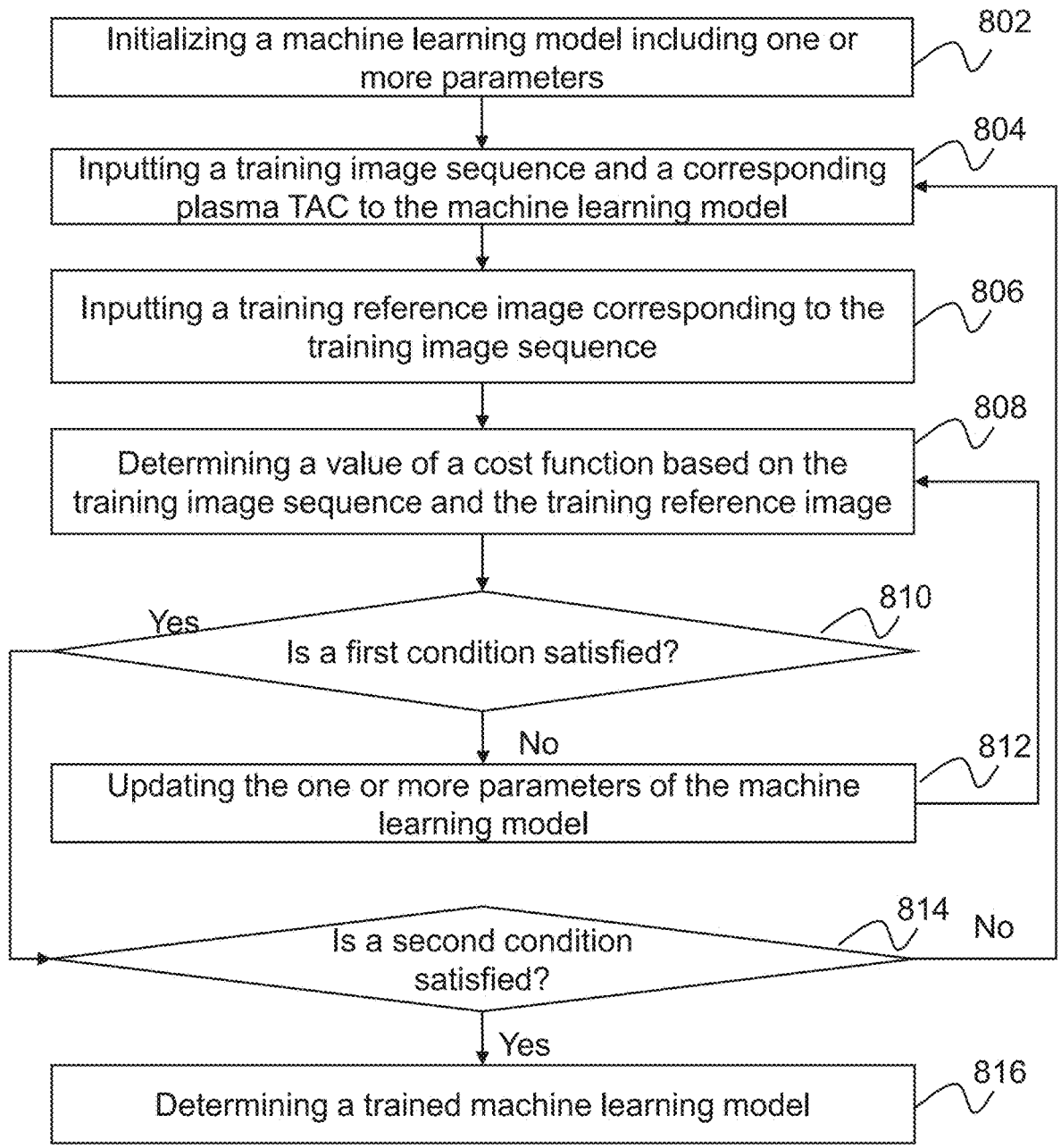
FIG. 8 is a flowchart illustrating an exemplary process for training a machine learning model according to some embodiments of the present disclosure.

FIG. 8 is a flowchart illustrating an exemplary process 800 for training a machine learning model according to some embodiments of the present disclosure. In some embodiments, one or more operations of process 800 illustrated in FIG. 8 may be implemented in the imaging system 100 illustrated in FIG. 1. For example, process 800 illustrated in FIG. 8 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). In some embodiments, one portion of operation 506 illustrated in FIG. 5 may be performed according to the process 700. For example, the target machine learning model as described in operation 506 may be determined according to process 800. In some embodiments, one portion of operation 608 illustrated in FIG. 6 may be performed according to the process 800. For example, the target machine learning model as described in operation 608 may be determined according to process 800. In some embodiments, operation 706 as illustrated in FIG. 7 may be performed according to process 800.

In 802, a machine learning model including one or more parameters may be initialized. Operation 802 may be performed by the model determination module 404. The machine learning model may be obtained as described in connection with operation 704.

In some embodiments, the one or more parameters of the machine learning model may include a plurality of architecture parameters and a plurality of learning parameters. Exemplary architecture parameters of the machine learning model may include the size of a convolutional kernel, the number of layers, the number of nodes in each layer, a learning rate, a minibatch size, an epoch, etc. Exemplary learning parameters of the machine learning model may include a connected weight between two connected nodes, a bias vector relating to a node, etc. The connected weight between two connected nodes may be configured to represent a proportion of an output value of a node to be as an input value of another connected node. In some embodiments, the connected weights of the machine learning model may be initialized to be random values in a range, e.g., the range from −1 to 1. In some embodiments, all the connected weights of the machine learning model may have a same value in the range from −1 to 1, for example, 0. The bias vector relating to a node may be configured to control an output value of the node deviating from an origin. In some embodiments, the bias vector of nodes in the machine learning model may be initialized to be random values in a range from 0 to 1. In some embodiments, the parameters of the machine learning model may be initialized based on a Gaussian random algorithm, a Xavier algorithm, etc.

In 804, an image sequence and a corresponding plasma TAC may be inputted into the machine learning model. Operation 804 may be performed by the model determination module 404. The image sequence and the corresponding plasma TAC may be obtained as described in connection with operation 702. For example, the image sequence may include one or more dynamic activity images, such as SUV images imaging a sample as described elsewhere in the present disclosure (e.g., FIG. 7 and the descriptions thereof). As another example, the corresponding plasma TAC may be determined based on the image sequence. The machine learning model may be obtained as described in connection with operation 704. More descriptions of the machine learning model may be found elsewhere in the present disclosure (e.g., FIGS. 5-7 and the descriptions thereof)

After inputting the image sequence and the corresponding plasma TAC into the machine learning model, the image sequence and the corresponding plasma TAC may be processed by multiple layers of the machine learning model to generate at least one portion of an estimated parametric image. During the training process, one or more first features may be extracted from the at least one portion of the estimated parametric image. The one or more first features may be related to values of one or more pixels or voxels of the at least one portion of the estimated parametric image. In some embodiments, the one or more first features may be extracted from the at least one portion of the estimated parametric image by the machine learning model (e.g., a convolution layer of the machine learning model). The one or more first features may include a low-level feature (e.g., an edge feature, a texture feature, etc.), a high-level feature (e.g., a semantic feature), or a complicated feature (e.g., a deep hierarchical feature) that is determined by the machine learning model.

In 806, a reference parametric image corresponding to the image sequence may be inputted into the machine learning model. Operation 806 may be performed by the model determination module 404. The reference parametric image may be obtained as described in connection with operation 706. For example, the reference parametric image may also be referred to as a parametric image, presenting a dynamic parameter associated with the same sample as the image sequence. The reference parametric image may be reconstructed using a four-dimensional (4D) iteration technique.

During the training process, one or more second features of the reference parametric image may be extracted from at least one portion of the reference parametric image. Each of the one or more second features may correspond to one of the one or more first features. As used herein, a second feature of a reference parametric image corresponding to a first feature of at least one portion of the estimated parametric image may refer to that the pixels or the voxels corresponding to the second feature and the pixels or the voxels corresponding to the first feature may be at the same position in the at least one portion of the estimated parametric image and the at least one portion of the reference parametric image, respectively. The second feature may include a low-level feature (e.g., an edge feature, a texture feature, etc.), a high-level feature (e.g., a semantic feature), a complicated feature (e.g., a deep hierarchical feature), etc., as described above.

Figure 9:
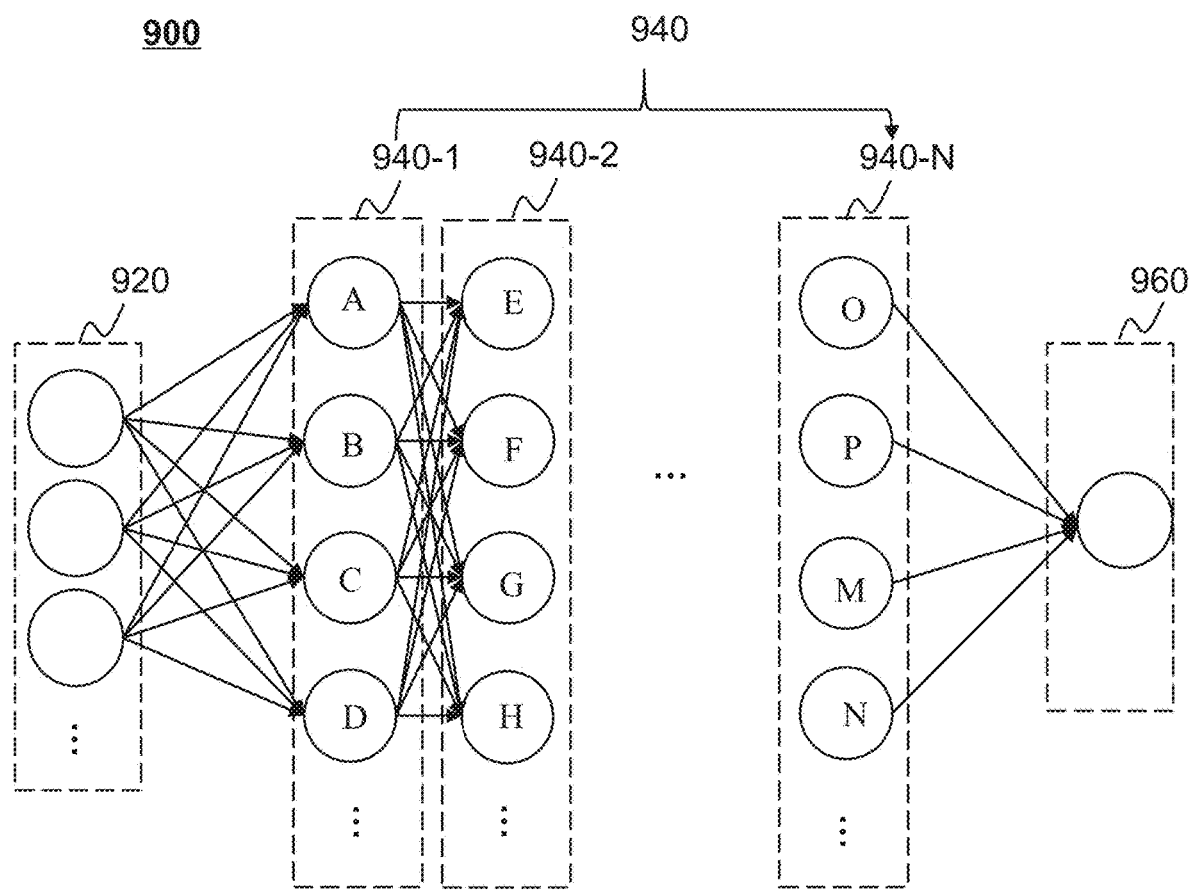
FIG. 9 is a schematic diagram illustrating an exemplary convolutional neural network (CNN) model according to some embodiments of the present disclosure.

In 808, a value of a cost function (also referred to as a loss function) may be determined based on the image sequence and the reference parametric image. Operation 808 may be performed by the model determination module 404. The cost function may be configured to assess a difference between an estimated value (e.g., at least one estimated parametric image) of the machine learning model and a desired value (e.g., the reference parametric image). For example, the cost function may be determined based on the one or more first features and the one or more second features. In some embodiments, the image sequence may be inputted to the machine learning model via an input layer (e.g., the input layer 920 as illustrated in FIG. 9), and then be transferred from a first hidden layer of the machine learning model (e.g., the convolution layers 940-1 as illustrated in FIG. 9) to the last hidden layer of the machine learning model. The image sequence may be processed in at least a portion of the multiple hidden layers to generate the at least one estimated parametric image. For example, the inputted image sequence may be processed by one or more convolution layer (e.g., the convolution layers 940-1 as illustrated in FIG. 9). The one or more convolution layers may be configured to perform an image transformation operation, an image enhancement operation, an image denoising operation, or any other operations on the image sequence based on the parameters relating to nodes in the one or more convolution layers. The at least one estimated parametric image processed by the hidden layers before the cost function layer may be inputted to the cost function layer. The value of the cost function layer may be determined based on the one or more first features and the one or more second features generated by the layers before the cost function layers via processing the at least one estimated parametric and the reference parametric image, respectively.

In 810, a determination may be made as to whether a first condition is satisfied. Operation 810 may be performed by the model determination module 404. If the first condition is satisfied, process 800 may proceed to operation 814. If the first condition is not satisfied, process 800 may proceed to 812. The first condition may provide an indication whether the machine learning model is sufficiently trained. In some embodiments, the first condition may relate to a value of the cost function. For example, the first condition may be satisfied if the value of the cost function is minimal or smaller than a threshold (e.g., a constant). As another example, the first condition may be satisfied if the value of the cost function converges. In some embodiments, convergence may be deemed to have occurred if the variation of the values of the cost function in two or more consecutive iterations is equal to or smaller than a threshold (e.g., a constant). In some embodiments, convergence may be deemed to have occurred if a difference between the value of the cost function and a target value is equal to or smaller than a threshold (e.g., a constant). In some embodiments, the first condition may be satisfied when a specified number of iterations relating to the first feature and the second feature are performed in the training process.

In 812, the one or more parameters of the machine learning model may be updated. Operation 812 may be performed by the model determination module 404. In some embodiments, at least one of the plurality of learning parameters may be adjusted. For example, the parameter value of at least some nodes may be adjusted until the value of the cost function relating satisfy the first condition. In some embodiments, the plurality of learning parameters of the machine learning model may be adjusted based on a back-propagation (BP) algorithm. Exemplary BP algorithms may include a stochastic gradient descent algorithm, an Adam algorithm, an Adagrad algorithm, an Adadelta algorithm, an RMSprop algorithm, or the like, or a combination thereof.

In 814, a determination may be made as to whether a second condition is satisfied. Operation 814 may be performed by the model determination module 404. If the second condition is satisfied, process 800 may proceed to 816. If the second condition is not satisfied, process 800 may return to 804 in which another image sequence may be extracted from a training set. The second condition may provide an indication whether the training may be terminated. In some embodiments, the second condition may be satisfied if a specified number of the image sequences and the reference parametric images are processed by the machine learning model or a specific count of iterations are performed.

In 816, a trained machine learning model may be determined. Operation 816 may be performed by the model determination module 404. In some embodiments, the trained machine learning model may be determined based on the updated parameters.

In some embodiments, process 800 may be repeated with respect to multiple training data including different groups of image sequences, plasma TACs, and the reference parametric images to improve or optimize the machine learning model until a termination condition is satisfied. In different rounds of process 800, different groups of image sequences and the reference parametric images may be inputted into the machine learning model. In some embodiments, the termination condition may be that a specific number of groups of image sequences and the reference parametric images have been analyzed. In some embodiments, the termination condition may be that a specific number of iterations have been performed.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, operations 804 and 806 may be omitted.

FIG. 9 is a schematic diagram illustrating an exemplary convolutional neural network (CNN) model 900 according to some embodiments of the present disclosure.

The CNN model may include an input layer 920, hidden layers 940, and an output layer 960. The multiple hidden layers 940 may include one or more convolutional layers, one or more Rectified Linear Units layers (ReLU layers), one or more pooling layers, one or more fully connected layers, or the like, or a combination thereof.

For illustration purposes, exemplary hidden layers 940 of the CNN model, including a convolutional layer 940-1, a pooling layer 940-2, and a fully connected layer 940-N, are illustrated. As described in connection with process 800, the model determination module 404 may acquire an image sequence and a plasma TAC as an input of the CNN model. The image sequence may be expressed as a 4D matrix including a plurality of elements (e.g., pixels or voxels). Each of the plurality of elements in the matrix may have a value (also referred to as pixel/voxel value) representing a characteristic of the element.

The convolutional layer 940-1 may include a plurality of kernels (e.g., A, B, C, and D). For example, the number of the plurality of kernels may be in a range from 16 to 64, for example, 32. The plurality of kernels may be used to extract features of a training sample (e.g., the image sequence, the plasma TAC, and the reference parametric image as described in FIG. 8). In some embodiments, each of the plurality of kernels may filter a portion (e.g., a region) of the image sequence to produce a specific feature corresponding to the portion of the image sequence. The feature may include a low-level feature (e.g., an edge feature, a texture feature, etc.), a high-level feature (e.g., a semantic feature), or a complicated feature (e.g., a deep hierarchical feature) that is calculated based on the kernel(s).

The pooling layer 940-2 may take the output of the convolutional layer 940-1 as an input. The pooling layer 940-2 may include a plurality of pooling nodes (e.g., E, F, G, and H). The plurality of pooling nodes may be used to sample the output of the convolutional layer 940-1, and thus may reduce the computational load of data processing and increase the speed of data processing of the imaging system 100. In some embodiments, the model determination module 404 may reduce the volume of the matrix corresponding to the image sequence in the pooling layer 940-2.

The fully connected layer 940-N may include a plurality of neurons (e.g., O, P, M, and N). The plurality of neurons may be connected to a plurality of nodes from the previous layer, such as a pooling layer. In the fully connected layer 940-N, the model determination module 404 may determine a plurality of vectors corresponding to the plurality of neurons based on the features of the training samples (e.g., the image sequences, the plasma TACs and the reference parametric image as described in FIG. 8) and further weigh the plurality of vectors with a plurality of weighting coefficients (i.e., connected weight).

In the output layer 960, the model determination module 404 may determine an output, such as a target image (e.g., parametric images), based on the plurality of vectors and weighting coefficients obtained in the fully connected layer 940-N.

It shall be noted that the CNN model may be modified when applied in different conditions. For example, in a training process, a loss function (also referred to as cost function in the disclosure) layer may be added to specify the deviation between an estimated output (e.g., at least one estimated parametric image) and a true label (e.g., a reference parametric image corresponding to the image sequence).

In some embodiments, the model determination module 404 may get access to multiple processing units, such as GPUs, in the imaging system 100. The multiple processing units may perform parallel processing in some layers of the CNN model. The parallel processing may be performed in such a manner that the calculations of different nodes in a layer of the CNN model may be assigned to two or more processing units. For example, one GPU may run the calculations corresponding to kernels A and B, and the other GPU(s) may run the calculations corresponding to kernels C and D in the convolutional layer 940-1. Similarly, the calculations corresponding to different nodes in other type of layers in the CNN model may be performed in parallel by the multiple GPUs.

EXAMPLE

The examples are provided for illustration purposes, and not intended to limit the scope of the present disclosure.

Example 1

Figure 10:
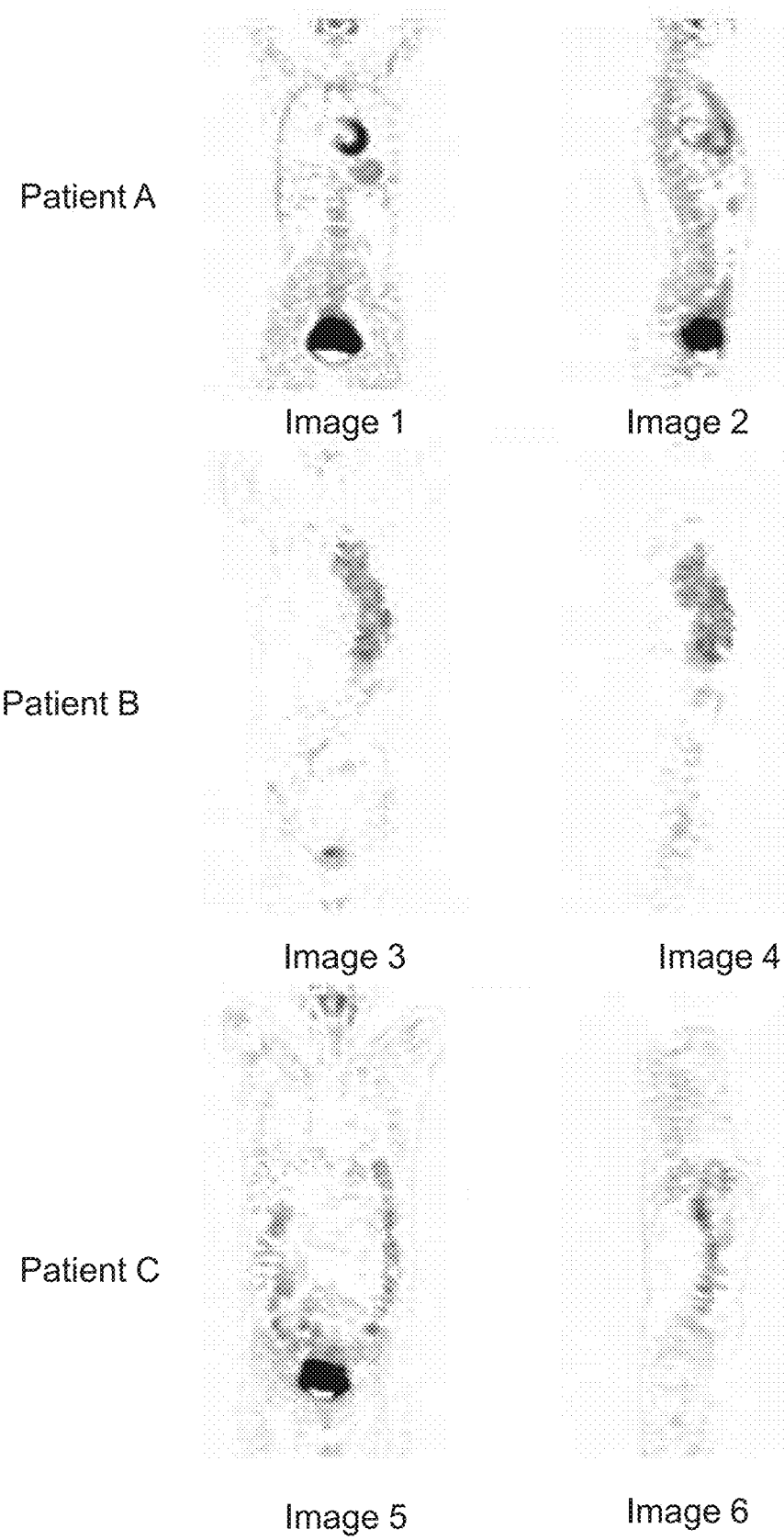
FIG. 10 shows exemplary torsos images of three patients reconstructed according to some embodiments of the present disclosure.

Exemplary PET Torsos Images of Patients Reconstructed Using a Linear Patlak Model FIG. 10 shows exemplary torsos images of three patients reconstructed according to some embodiments of the present disclosure. As shown in FIG. 10, Image 1-6 are parametric images reconstructed based on SUV images using a linear Patlak model. The SUV images may be reconstructed using a 3D iterative algorithm (e.g., the MLEM algorithm, the OSEM algorithm). Image 1 and Image 2 are a coronal view and a sagittal view of the torso of patient A, respectively. Image 3 and Image 4 are a coronal view and a sagittal view of the torso of patient B, respectively. Image 5 and Image 6 are a coronal view and a sagittal view of the torso of patient C, respectively.

Example 2

Figure 11:
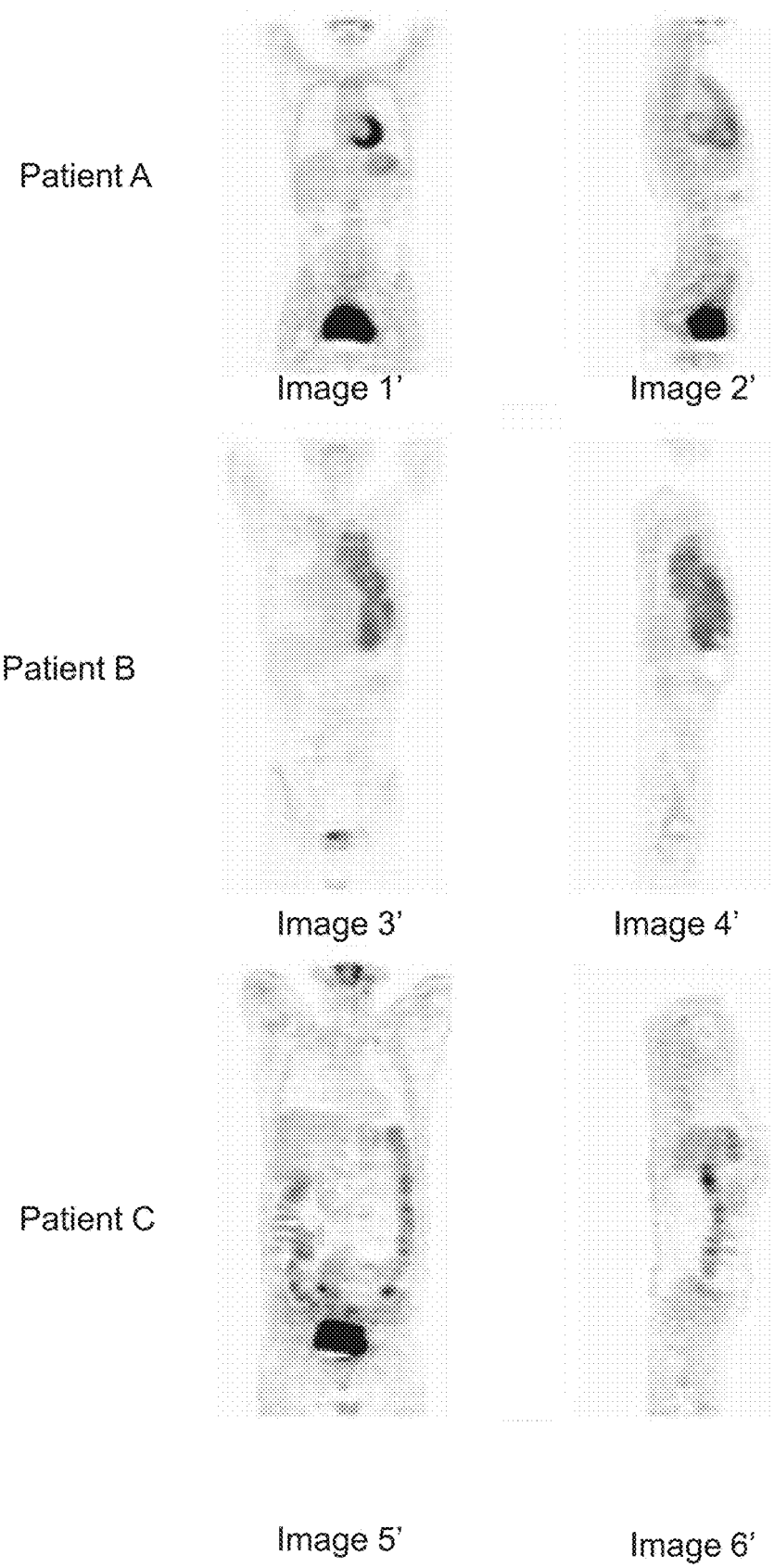
FIG. 11 shows exemplary torsos images of three patients described in FIG. 10 reconstructed according to some embodiments of the present disclosure.

Exemplary PET Torsos Images of Three Patients Reconstructed Using a 4D Iteration Technique FIG. 11 shows exemplary images of the torsos of three patients described in FIG. 10 reconstructed according to some embodiments of the present disclosure. As shown in FIG. 11, Image 1'-6' are parametric images reconstructed using a 4D iterative technique as described in operation 702. Image 1'-6' correspond to Image 1-6 as described in FIG. 10, respectively.

Example 3

Figure 12:
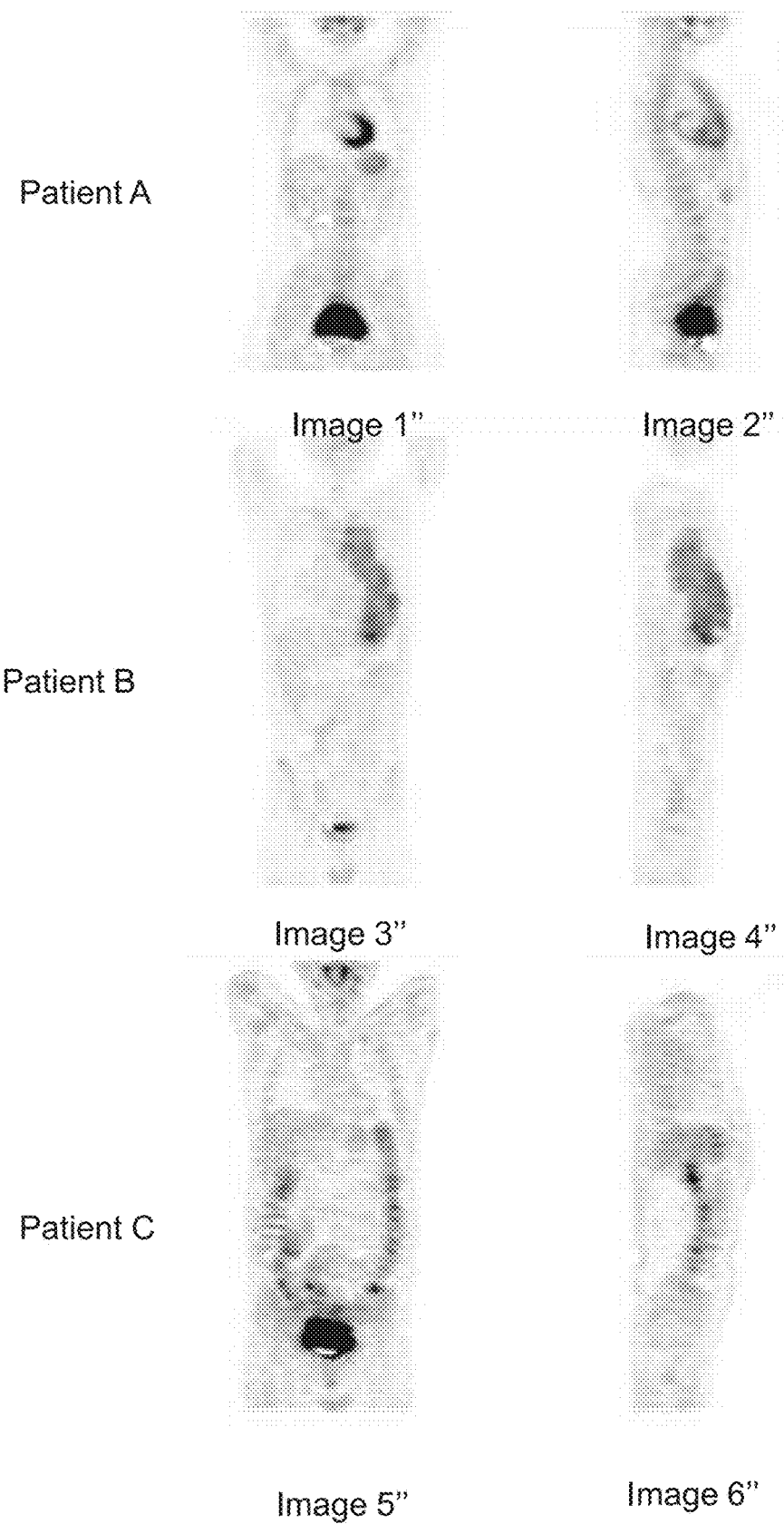
FIG. 12 shows exemplary torsos images of three patients described in FIG. 10 reconstructed according to some embodiments of the present disclosure.

Exemplary PET Torsos Images of Three Patients Reconstructed Using a Target Machine Learning Model FIG. 12 shows exemplary torsos images of three patients described in FIG. 10 reconstructed according to some embodiments of the present disclosure. As shown in FIG. 12, Image 1"-6" are parametric images reconstructed using a target machine learning model according to process 500 and/or 600. Image 1"-6" correspond to Image 1-6 as described in FIG. 10 and Image 1'-6' as described in FIG. 11, respectively.

As shown in FIG. 10, FIG. 11 and/or FIG. 12, Image 1"-6" reconstructed using the target machine learning model in FIG. 12 are more similar or close to corresponding Image 1'-6', respectively, reconstructed using the 4D iteration technique in FIG. 11 than corresponding Image 1-6, respectively, reconstructed using the linear Patlak model in FIG. 10. As used herein, Image 1" are more similar or close to Image 1' than Image 1 may refer to that a similarity between the Image 1' and Image 1" are greater than a similarity between the Image 1' and Image 1.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB, NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for image reconstruction, comprising:
   at least one storage device storing executable instructions, and at least one processor in communication with the at least one storage device, when executing the executable instructions, causing the system to:
obtain an image sequence associated with a subject, the image sequence including one or more images generated via scanning the subject at one or more consecutive time periods;
obtain a plasma time activity curve associated with the subject;
obtain a target machine learning model; and
generate, based on the image sequence and the plasma time activity curve, at least one target image using the target machine learning model, the at least one target image presenting a dynamic parameter associated with the subject, wherein the target machine learning model provides a mapping between the image sequence and the at least one target image.

2. The system of claim 1, wherein to generate, based on the image sequence, the at least one target image using target machine learning model, the at least one processor is further configured to direct the system to:
input the image sequence associated with the subject into the target machine learning model; and
convert the image sequence into the at least one target image.

3. The system of claim 1, wherein to obtain the plasma time activity curve associated with the subject, the at least one processor is further configured to direct the system to:
obtain, based on the image sequence, the plasma time activity curve associated with the subject using an additional target machine learning model, wherein the additional target machine learning model provides a mapping between the image sequence and the plasma time activity curve.

4. The system of claim 1, wherein a determination of the target machine learning model includes:
obtaining multiple groups of training data associated one or more samples, each group of the multiple groups of training data including a first image sequence and a first parametric image corresponding to the first image sequence, the first parametric image presenting the dynamic parameter associated with one of the one or more samples; and
generating the target machine learning model by training a machine learning model using the multiple groups of training data.

5. The system of claim 4, wherein the obtaining multiple groups of training data associated one or more samples includes:
for each group of the multiple groups of training data, obtaining projection data associated with the one of the one or more samples;
generating, based on the projection data, the first image sequence using a first image reconstruction algorithm; and
generating, based on the projection data, the first parametric image using a second image reconstruction algorithm.

6. The system of claim 5, wherein the second image reconstruction algorithm includes a four-dimensional (4D) iteration technique.

7. The system of claim 4, wherein the determination of the target machine learning model further includes:
obtaining a reference plasma time activity curve associated with the one of the one or more samples, wherein the generating the target machine learning model by training the machine learning model using the multiple groups of training data includes:
training, based on the reference plasma time activity curve, the machine learning model using the multiple groups of training data.

8. The system of claim 7, wherein the reference plasma time activity curve associated with the one of the one or more samples is determined based on the training image sequence associated with the one of the one or more samples.

9. The system of claim 4, wherein the determination of the target machine learning model further includes:
obtaining multiple groups of validation data, each group of the multiple groups of validation data including a second image sequence and a second parametric image corresponding to the second image sequence, the second parametric image presenting the dynamic parameter; and
adjusting the target machine learning model using the multiple groups of validation data.

10. The system of claim 1, wherein the target machine learning model is constructed based on a deep learning neural network model.

11. The system of claim 1, wherein the deep learning neural network model includes a convolution neural network (CNN) model.

12. The system of claim 1, wherein to obtain the plasma time activity curve associated with the subject, the at least one processor is further configured to direct the system to:
determine the plasma time activity curve using a gold standard technique, an arterialization of venous blood technique, a Positron Emission Tomography (PET) blood pool scan technique, a standard input function technique, a fitting function technique, or the like, or a combination thereof.

13. A method for image reconstruction implemented on a computing apparatus, the computing apparatus including at least one processor and at least one storage device, the method comprising:
obtaining an image sequence associated with a subject, the image sequence including one or more images generated via scanning the subject at one or more consecutive time periods;
obtaining a plasma time activity curve associated with the subject;
obtaining a target machine learning model; and
generating, based on the image sequence and the plasma time activity curve, at least one target image using the target machine learning model, the at least one target image presenting a dynamic parameter associated with the subject, wherein the target machine learning model provides a mapping between the image sequence and the at least one target image.

14. The method of claim 13, wherein generating, based on the image sequence, the at least one target image using target machine learning model further includes:
inputting the image sequence associated with the subject into the target machine learning model; and
converting the image sequence into the at least one target image.

15. The method of claim 13, wherein obtaining the plasma time activity curve associated with the subject further includes:
obtaining, based on the image sequence, the plasma time activity curve associated with the subject using an additional target machine learning model, wherein the additional target machine learning model provides a mapping between the image sequence and the plasma time activity curve.

16. The method of claim 13, wherein a determination of the target machine learning model includes:
   obtaining multiple groups of training data associated one or more samples, each group of the multiple groups of training data including a first image sequence and a first parametric image corresponding to the image sequence, the first parametric image presenting the dynamic parameter associated with one of the one or more samples; and
   generating the target machine learning model by training a machine learning model using the multiple groups of training data.

17. The method of claim 16, wherein the determination of the target machine learning model further includes:
   obtaining a reference plasma time activity curve associated with the one of the one or more samples, wherein the generating the target machine learning model by training the machine learning model using the multiple groups of training data includes:
   training, based on the reference plasma time activity curve, the machine learning model using the multiple groups of training data.

18. The method of claim 13, wherein the determination of the target machine learning model further includes:
   obtaining multiple groups of validation data, each group of the multiple groups of validation data including a second image sequence and a second parametric image corresponding to the second image sequence, the second parametric image presenting the dynamic parameter; and
   adjusting the target machine learning model using the multiple groups of validation data.

19. A non-transitory computer-readable medium storing at least one set of instructions, wherein when executed by at least one processor, the at least one set of instructions directs the at least one processor to perform acts of:
   obtaining an image sequence associated with a subject, the image sequence including one or more images generated via scanning the subject at one or more consecutive time periods;
   obtaining a plasma time activity curve associated with the subject;
   obtaining a target machine learning model; and
   generating, based on the image sequence and the plasma time activity curve, at least one target image using the target machine learning model, the at least one target image presenting a dynamic parameter associated with the subject, wherein the target machine learning model provides a mapping between the image sequence and the at least one target image.

20. The method of claim 13, wherein obtaining the plasma time activity curve associated with the subject further includes: determining the plasma time activity curve using a gold standard technique, an arterialization of venous blood technique, a Positron Emission Tomography (PET) blood pool scan technique, a standard input function technique, a fitting function technique, or the like, or a combination thereof.

* * * * *